(12) United States Patent
Abe et al.

(10) Patent No.: US 7,374,923 B2
(45) Date of Patent: May 20, 2008

(54) POLYPEPTIDE

(75) Inventors: Kunitake Abe, Ibaraki (JP); Masayoshi Takeda, Ibaraki (JP); Noboru Yamaji, Ibaraki (JP); Miyuki Katou, Ibaraki (JP); Tetsuo Matsui, Ibaraki (JP)

(73) Assignee: Astellas Pharma Inc., Tokyo (JP)

( * ) Notice: Subject to any disclaimer, the term of this patent is extended or adjusted under 35 U.S.C. 154(b) by 31 days.

(21) Appl. No.: 11/593,512

(22) Filed: Nov. 7, 2006

(65) Prior Publication Data

US 2007/0077591 A1    Apr. 5, 2007

Related U.S. Application Data

(62) Division of application No. 10/491,277, filed as application No. PCT/JP03/01788 on Feb. 19, 2003, now Pat. No. 7,157,567.

(30) Foreign Application Priority Data

Feb. 20, 2002 (JP) ............... 2002-43533
Sep. 19, 2002 (JP) ............... 2002-273603

(51) Int. Cl.
*C12N 9/64* (2006.01)
*C12N 15/57* (2006.01)
*C12N 15/79* (2006.01)

(52) U.S. Cl. ............... 435/226; 435/69.1; 435/252.3; 435/320.1; 526/23.2

(58) Field of Classification Search ............... None
See application file for complete search history.

(56) References Cited

U.S. PATENT DOCUMENTS

| 6,458,552 | B1* | 10/2002 | Fourie et al. ............... 435/23 |
| 6,683,165 | B1 | 1/2004 | Keith et al. |
| 6,900,016 | B1 | 5/2005 | Venter et al. |
| 7,226,596 | B2* | 6/2007 | Bodary et al. ............ 424/181.1 |
| 2002/0132237 | A1 | 9/2002 | Algate et al. |
| 2003/0170228 | A1 | 9/2003 | Ashkenazi et al. |
| 2003/0175900 | A1* | 9/2003 | Ashkenazi et al. ......... 435/71.2 |
| 2003/0211096 | A1* | 11/2003 | Ashkenazi et al. ...... 424/130.1 |
| 2005/0003390 | A1 | 1/2005 | Axenovich et al. |
| 2005/0089957 | A1* | 4/2005 | Goddard et al. ............ 435/69.1 |
| 2006/0024692 | A1 | 2/2006 | Nakamura et al. |

FOREIGN PATENT DOCUMENTS

| WO | WO 01/09189 | 2/2001 |
| WO | WO 01/53486 | 7/2001 |
| WO | WO 01/92581 | 12/2001 |
| WO | WO 03/018621 | 5/2003 |
| WO | WO 03/034984 | 5/2003 |

OTHER PUBLICATIONS

Yoshiyama et al, *Genomics*, 41:56-62 (1997).
Kataoka et al, *J. Biol. Chem.*, 272:18209-18215 (1997).
Yoshida et al, *Int. Immunol.*, 2:585-591 (1990).

* cited by examiner

*Primary Examiner*—Nashaat T. Nashed
*Assistant Examiner*—William W. Moore
(74) *Attorney, Agent, or Firm*—Sughrue Mion, PLLC.

(57) ABSTRACT

A screening tool and a screening method for a therapeutic agent for type II diabetes, particularly an agent for alleviating insulin resistance are disclosed. A novel polypeptide, a polynucleotide, a vector, a promoter, and a transformant which are useful in the screening tool and the screening method, are also disclosed.

2 Claims, 2 Drawing Sheets

1 2 3 4 5 6 7

POLYPEPTIDE

CROSS-REFERENCE TO RELATED APPLICATIONS

This application is a Divisional of U.S. application Ser. No. 10/491,277 filed Mar. 31, 2004, which issued as U.S. Pat. No. 7,157,567 on Jan. 2, 2007; which is a 371 of PCT/JP03/01788, filed Feb. 19, 2003; the entire disclosure of each of these applications is incorporated herein by reference.

TECHNICAL FIELD

This invention relates to a novel polypeptide useful when screening a therapeutic agent for type II diabetes, particularly an agent for alleviating insulin resistance, and to a screening tool and a screening method for a therapeutic agent for type II diabetes, particularly an agent for alleviating insulin resistance.

BACKGROUND ART

The number of people diagnosed as diabetic is increasing, due to insufficient exercise or a westernization of life style, such as a habit of eating a high fat diet. Diabetes which more than 90% of patients are suffering from are type II diabetes, characterized by a deficiency of insulin action caused by an increase of insulin resistance or a decrease of insulin secretion.

In a healthy person, when the blood glucose level is increased by food ingestion, insulin secreted from the pancreas is rapidly increased. In response to the resultant insulin concentration, an action of decreasing the glucose release in the liver and an action of increasing the glucose uptake in skeletal muscles and adipose tissues occur, and thus the blood glucose level is decreased and returns to the normal level. However, in a patient suffering from type II diabetes exhibiting an insulin resistance, due to a low sensibility to insulin in tissues, a decrease of the glucose release in the liver or an increase of the glucose uptake in muscles and adipose tissues in response to insulin is not sufficient, and thus abnormal changes in the blood glucose level, such as postprandial hyperglycemia or fasting hyperglycemia, is observed. After the developing of diabetes, the diabetes progresses without subjective symptoms for a long time. Because complications, such as diabetic retinopathy, diabetic nephropathy, or neuropathy, supervene in severe diabetes, it is very important to prevent or treat diabetes at an early stage.

As therapeutic agents for diabetes capable of alleviating insulin resistance, biguanides, which increase the action of inhibiting glucose release in the liver as the main effect, or thiazoline derivatives, which decrease the insulin resistance in the liver, fat, and/or skeletal muscles as the main effect, are clinically used. However, a cautious administration is required due to complications, side effects, or the like, and thus a more efficient agent exhibiting no side effects is desired for alleviating insulin resistance (non-patent reference 1).

The decreased insulin action to glucose metabolism is commonly observed in type II diabetes, and closely involved in abnormal glucose metabolism in the whole body. Therefore, a pathological clarification of type II diabetes and development of therapeutic agents therefor must clarify a mechanism of promoting glucose transport by insulin (non-patent reference 2). In other words, a factor which inhibits the glucose transport mechanism is probably involved in diabetes.

Insulin and insulin-like growth factor I (IGF-I) are peptide hormones belonging to the same family, and are highly similar in structure and functions. Further, the insulin receptor and IGF-I receptor are homologous molecules belonging to a tyrosine kinase-type receptor family, and each native ligand thereof exhibits a cross-reactivity for the other receptor (non-patent reference 3). It is known that a signal transduction is promoted by binding insulin or IGF-1 with the receptor thereof, and that a glucose uptake from extracellular fluid causes an action of decreasing blood glucose (non-patent reference 4). IGF-I alone is not stable in blood, and more than 90% thereof forms complexes with insulin-like growth factor binding protein (IGFBP), to maintain stability, and thus it is considered that the existence of IGFBP is important from the viewpoint of tissue delivery or control of the action (non-patent reference 5). Many reports on the relationship between diabetes and IGFBP have been made, and it is known, for example, that IGFBP-3 and IGFBP-5 are decreased in the blood of patients suffering from type I/II diabetes (non-patent reference 6), that an N-terminus undigested product (18 kDa) of IGFBP-3 is increased in the urine of patients suffering from type I diabetes (non-patent reference 7), that when streptozotocin, which specifically destroys pancreatic β cells and can cause diabetes by experimentally administering it to an animal, is administered to rat to induce diabetes, IGFBP-3 is expressed together with IGFBP-5 in renal glomeruli (non-patent reference 8), that a positive correlation between an activity of digesting IGFBP-3 in the urine of patients suffering from type II diabetes with diabetic nephropathy and an amount of albumin leaked into the urine of patients suffering from diabetic nephropathy is observed (non-patent reference 9), that a polymorphism of causes of type I diabetes exists near the IGFBP-2 and IGFBP-5 genes (non-patent reference 10), and that when IGFBP-3 is digested by protease, the affinity thereof for IGF-I is decreased and the affinity of the digested N-terminus fragment for insulin is increased (non-patent reference 11 and non-patent reference 12).

As described above, it is considered that an effective method for treating diabetes (alleviating insulin resistance) can be also provided by inhibiting IGFBP digestion.

In this connection, the deduced amino acid sequence of human ADAM8 is known, and it is suggested that human ADAM8 is metalloprotease and is involved in tumors and platelet aggregation (patent reference 1, patent reference 2, non-patent reference 13, non-patent reference 14, and non-patent reference 15). However, a relationship between human ADAM8 and diabetes is not suggested.

(non-patent reference 1) Ryuzo Kawamori et al., "Tonyoubyou 2001 Karada no Kagaku, zoukan (supplement)", Nippon-Hyoron-sha, 2001, p.86-108

(non-patent reference 2) Oka, "Saishin Igaku (The Medical Frontline )", 2002, p.41-46

(non-patent reference 3) Miyazono et al., "Saitokain & zoshoku Inshi (Cytokines and growth factors)", YODOSHA, 104-109, 1998

(non-patent reference 4) Kadowaki et al., "Medical terms libraly, diabetes", YODOSHA, 52-53, 1995

(non-patent reference 5) Yamanaka et al., "Horumon to Rinsho (CLINCAL ENDOCRINOLOGY)", 29-38, 1998

(non-patent reference 6) J. Endocrinol., 159, 297-306, 1998

(non-patent reference 7) Clinical Endocrinology, 51, 587-596, 1999

(non-patent reference 8) Am. J. Kidney. diseases, 1000-1010,
(non-patent reference 9) J. Clin. Endo. Metab., 85, 1163-1169, 2000
(non-patent reference 10) Science, 272, 1811-1813, 1996
(non-patent reference 11) Yamanaka Y. et al., J. Biol. Chem., 272, 30729-30734, 1997
(non-patent reference 12) Peter V. et al., J. Clin. Endocrinol. Metab., 83, 1392-1395,1998
(non-patent reference 13) SWISSPROT P78325 AD08 HUMAN(1997.11.1) available on the internet at kr.expasy.org/cgi-bin/niceprot.pl?P78325
(non-patent reference 14) NCBI D265791 Homo sapiens mRNA (1999.2.6) available on the internet at ncbi.nlm.nih.gov/entrez/query.fcgi?cmd=Retrieve&db=nucleotide&list_uids=1864004&dopt=GenBank
(non-patent reference 15) Genomics 1997 Apr. 1 41, 56 CD156
(human ADAM8)
(patent reference 1) WO01/09189
(patent reference 2) WO01/53486

DISCLOSURE OF INVENTION

The present inventors conducted intensive studies into the provision of a screening system for obtaining a novel agent for alleviating insulin resistance and, as a result, found a gene of which the expression was increased in a diabetes model mouse and obtained the gene (mouse MD8 gene), a human ortholog gene (human MD8 gene), and a promoter of the human MD8 gene. Further, the present inventors found that an overexpression of the mouse MD8 or human MD8 in adipocytes inhibits glucose uptake by an insulin stimulation, and that human MD8 is a novel protease having an activity of digesting IGFBP. In this connection, it is considered that insulin resistance is increased by digesting IGFBP. On the basis of these findings, the present inventors clarified that MD8 and the promoter thereof can be used as a tool useful when screening a novel therapeutic agent for diabetes (particularly an agent for alleviating insulin resistance), and provided a novel screening tool and screening method for a novel therapeutic agent for diabetes (particularly an agent for alleviating insulin resistance) and a novel method for manufacturing a novel pharmaceutical composition for treating diabetes (particularly an agent for alleviating insulin resistance), and thus the present invention was completed.

The present invention relates to:

[1] a screening tool for a therapeutic agent for diabetes, wherein the tool is
(1) a polypeptide consisting of the amino acid sequence of SEQ ID NO: 2 or SEQ ID NO: 14,
(2) a polypeptide exhibiting an activity of inhibiting glucose uptake into an adipocyte by an insulin stimulation, and comprising an amino acid sequence in which 1 to 10 amino acids are deleted, substituted, and/or inserted in the amino acid sequence of SEQ ID NO: 2 or SEQ ID NO: 14,
(3) a polypeptide exhibiting an activity of inhibiting glucose uptake into an adipocyte by an insulin stimulation, and comprising the amino acid sequence of SEQ ID NO: 2 or SEQ ID NO: 14, or
(4) a polypeptide exhibiting an activity of inhibiting glucose uptake into an adipocyte by an insulin stimulation, and consisting of an amino acid sequence having an 80% or more homology with that of SEQ ID NO: 2 or SEQ ID NO: 14;

[2] the screening tool for a therapeutic agent for diabetes of [1], wherein the tool is (1) a polypeptide consisting of the amino acid sequence of SEQ ID NO: 2 or SEQ ID NO: 14;
[3] a screening tool for a therapeutic agent for diabetes, wherein the tool is a cell expressing the polypeptide of [1] or [2];
[4] the screening tool for a therapeutic agent for diabetes of [3], wherein the cell is a transformant;
[5] a screening tool for a therapeutic agent for diabetes, wherein the tool is
(1) a polynucleotide consisting of the base sequence consisting of the 34th to 2014th bases in the base sequence of SEQ ID NO: 20,
(2) a polynucleotide exhibiting a promoter activity of the polypeptide of [1] or [2], and comprising a base sequence in which one or more bases are substituted, deleted, and/or inserted at 1 to 10 positions in the base sequence consisting of the 34th to 2014th bases in the base sequence of SEQ ID NO: 20,
(3) a polynucleotide exhibiting a promoter activity of the polypeptide of [1] or [2], and comprising at least a part of the base sequence consisting of the 34th to 2014th bases in the base sequence of SEQ ID NO: 20, or
(4) a polynucleotide exhibiting a promoter activity of the polypeptide of [1] or [2], and hybridizing under stringent conditions to a polynucleotide consisting of the base sequence consisting of the 34th to 2014th bases in the base sequence of SEQ ID NO: 20;
[6] the screening tool for a therapeutic agent for diabetes of [5], wherein the polypeptide exhibits a promoter activity of the polypeptide of [1] or [2], and comprises the base sequence consisting of the 34th to 2014th bases in the base sequence of SEQ ID NO: 20;
[7] a screening tool for a therapeutic agent for diabetes, wherein the tool is a cell comprising the polynucleotide of [5] or [6];
[8] the screening tool for a therapeutic agent for diabetes of [7], wherein the cell is a transformant;
[9] the screening tool or [1] to [8], wherein the therapeutic agent for diabetes is an agent for alleviating insulin resistance;
[10] a method for analyzing whether or not a substance to be tested is an inhibitor of the polypeptide of [1] or [2], comprising the steps of:
bringing a cell expressing the polypeptide of [1] or [2] into contact with the substance to be tested, and analyzing an amount of glucose uptake by an insulin stimulation;
[11] a method for screening an inhibitor of the polypeptide of [1] or [2], comprising the steps of:
analyzing a substance to be tested by the method of [10], and selecting an inhibitor;
[12] a method for screening a therapeutic agent for diabetes, comprising the steps of:
analyzing a substance to be tested by the method of [10], and selecting an inhibitor;
[13] a method for analyzing whether or not a substance to be tested inhibits a promoter activity of the polynucleotide of [5]or [6], comprising the steps of:
(1) bringing the cell of [7] or [8] into contact with the substance to be tested, and
(2) analyzing the promoter activity;
[14] a method for screening a substance which inhibits an expression of the polypeptide of [1] or [2], comprising the steps of:
analyzing a substance to be tested by the method of [13], and selecting a substance which inhibits the promoter;

[15] a method for screening a therapeutic agent for diabetes, comprising the steps of:

analyzing a substance to be tested by the method of [13], and selecting a substance which inhibits the promoter activity;

[16] a process for manufacturing a pharmaceutical composition for treating diabetes, comprising the steps of:

analyzing a substance to be tested by the method of [10] or [13], and preparing a medicament containing the substance;

[17] a polypeptide exhibiting an activity of inhibiting glucose uptake into an adipocyte by an insulin stimulation, and comprising the amino acid sequence of SEQ ID NO: 2;

[18] a polypeptide consisting of the amino acid sequence of SEQ ID NO: 2;

[19] a polynucleotide encoding the polypeptide of [17] or [18];

[20] a vector expressibly comprising the polynucleotide of [19];

[21] a transformant comprising the polynucleotide of [19];

[22] (1) a polynucleotide consisting of the base sequence consisting of the 34th to 2014th bases in the base sequence of SEQ ID NO: 20, (2) a polynucleotide exhibiting a promoter activity of the polypeptide of [1] or [2], and comprising a base sequence in which one or more bases are substituted, deleted, and/or inserted at 1 to 10 positions in the base sequence consisting of the 34th to 2014th bases in the base sequence of SEQ ID NO: 20, (3) a polynucleotide exhibiting a promoter activity of the polypeptide of [1] or [2], and comprising at least a part of the base sequence consisting of the 34th to 2014th bases in the base sequence of SEQ ID NO: 20, or (4) a polynucleotide exhibiting a promoter activity of the polypeptide of [1] or [2], and hybridizing under stringent conditions to a polynucleotide consisting of the base sequence consisting of the 34th to 2014th bases in the base sequence of SEQ ID NO: 20;

[23] the polynucleotide of [22], exhibiting a promoter activity of the polypeptide of [1] or [2], and comprising the base sequence consisting of the 34th to 2014th bases in the base sequence of SEQ ID NO: 20;

[24] a transformant comprising the polynucleotide of [22] or [23];

[25] a method for producing the polypeptide of [17] or [18], comprising the step of:

culturing the transformant of [21]; and

[26] a probe which hybridizes to the polynucleotide of [19] under stringent conditions[19].

The present invention includes use of the polypeptide of [1] or [2], the cell of [3], [4], [7], or [8], and the polynucleotide of [5] or [6] for screening a therapeutic agent for diabetes. As the "therapeutic agent for diabetes", an agent for alleviating insulin resistance is preferable. The "therapeutic agent for diabetes" or "pharmaceutical composition for treating diabetes" includes both an agent or pharmaceutical composition used for treating a patient suffering from diabetes and that preventively used for a subject exhibiting signs of diabetes.

BEST MODE FOR CARRYING OUT THE INVENTION

Figure 1:
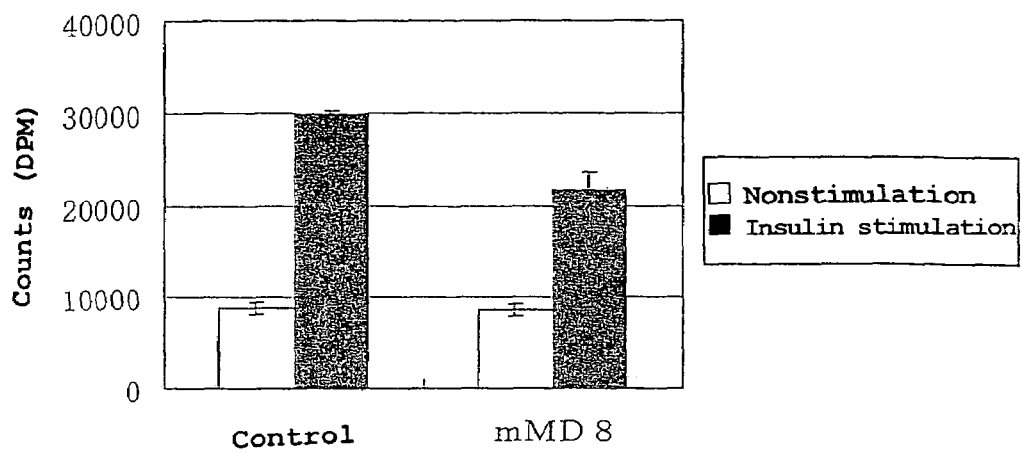
FIG. 1 is a graph showing amounts of glucose uptake by an insulin stimulation in differentiated adipocytes infected with the mMD8 virus or control virus.

The present invention will be explained in detail hereinafter.

Genetic recombination techniques may be performed in accordance with known methods (for example, "Molecular Cloning-A Laboratory Manual", Cold Spring Harbor Laboratory, N.Y., 1989; or WO01/34785).

1. Screening Tool of the Present Invention

The screening tool of the present invention for a therapeutic agent for diabetes, particularly an agent for alleviating insulin resistance, includes a polypeptide-type screening tool, cell-type screening tool, and promoter-type screening tool.

(1) Polypeptide-type Screening Tool

As the polypeptide which may be used as the polypeptide-type screening tool of the present invention, there may be mentioned, for example, (i) a polypeptide consisting of the amino acid sequence of SEQ ID NO: 2 or SEQ ID NO: 14;

(ii) (a) a polypeptide exhibiting an activity of inhibiting glucose uptake into an adipocyte by an insulin stimulation, and comprising an amino acid sequence in which 1 to 10 amino acids are deleted, substituted, and/or inserted in the amino acid sequence of SEQ ID NO: 2 or SEQ ID NO: 14; or (b) a polypeptide exhibiting an activity of inhibiting glucose uptake into an adipocyte by an insulin stimulation, and comprising the amino acid sequence of SEQ ID NO: 2 or SEQ ID NO: 14 (hereinafter referred to as a variation functionally equivalent); or (iii) a polypeptide exhibiting an activity of inhibiting glucose uptake into an adipocyte by an insulin stimulation, and consisting of an amino acid sequence having a 80% or more homology with that of SEQ ID NO: 2 or SEQ ID NO: 14 (hereinafter referred to as a homologous polypeptide).

Hereinafter, the polypeptides which may be used as the polypeptide-type screening tool of the present invention are collectively referred to as polypeptides for a screening tool.

The "polypeptide consisting of the amino acid sequence of SEQ ID NO: 2" (hereinafter sometimes referred to as MD8 protein) and the "polypeptide consisting of the amino acid sequence of SEQ ID NO: 14" (hereinafter sometimes referred to as mMD8 protein), which are polypeptides of the present invention for a screening tool, are a novel human polypeptide consisting of 824 amino acid residues and a mouse polypeptide consisting of 825 amino acid residues, respectively. The MD8 protein and MMD8 protein are metalloproteases having a zinc-coordinated consensus sequence (HExxH: SEQ ID NO: 15).

The polypeptide consisting of the amino acid sequence of SEQ ID NO: 2 or 14 exhibits an activity of inhibiting glucose uptake into an adipocyte by an insulin stimulation.

"To exhibit an activity of inhibiting glucose uptake into an adipocyte by an insulin stimulation" as used herein means, when an adipocyte expressing a polypeptide as a target and an adipocyte without expressing the polypeptide are independently stimulated by insulin and then amounts of glucose uptake in the adipocytes are compared, to decrease the amount of glucose uptake in the adipocyte expressing the polypeptide. Comparison of the amounts of glucose uptake by an insulin stimulation can be performed, for example, in accordance with methods described in Examples 4-7. As the degree of the decrease of glucose uptake, 20% or more is preferable, 50% or more is more preferable, and 80% or more is most preferable.

As the variation functionally equivalent which may be used as the polypeptide-type screening tool of the present invention, (a) a polypeptide exhibiting an activity of inhibiting glucose uptake into an adipocyte by an insulin stimulation, and consisting of an amino acid sequence in which 1 to 10 (preferably 1 to 7, more preferably 1 to 5) amino acids in total are deleted, substituted, inserted, and/or added at one or plural positions in the amino acid sequence of SEQ ID NO: 2 or SEQ ID NO: 14; or (b) a polypeptide exhibiting an activity of inhibiting glucose uptake into an adipocyte by an insulin stimulation, and comprising the amino acid sequence of SEQ ID NO: 2 or SEQ ID NO: 14 are preferable.

The polypeptides exhibiting an activity of inhibiting glucose uptake into an adipocyte by an insulin stimulation, and comprising the amino acid sequence of SEQ ID NO: 2 or SEQ ID NO: 14 include, for example, a polypeptide in which an appropriate marker sequence or the like is added to the N-terminus and/or the C-terminus of the polypeptide consisting of the amino acid sequence of SEQ ID NO: 2 or SEQ ID NO: 14 (i.e., a fusion polypeptide), so long as the fusion polypeptide exhibits an activity of inhibiting glucose uptake into an adipocyte by an insulin stimulation.

As the marker sequence, for example, a sequence for easily carrying out a confirmation of polypeptide expression, confirmation of intracellular localization thereof, purification thereof, or the like may be used. As the sequence, there may be mentioned, for example, the FLAG epitope, the hexa-histidine tag, the hemagglutinin tag, the myc epitope, or the like.

The homologous polypeptide which may be used as the polypeptide-type screening tool of the present invention may consist of an amino acid sequence having preferably a 90% or more homology, more preferably a 95% or more homology, still further preferably a 98% or more homology, most preferably a 99% or more homology, with respect to the amino acid sequence of SEQ ID NO: 2 or SEQ ID NO: 14.

The term "homology" as used herein means a value obtained by a BLAST (Basic local alignment search tool; Altschul, S. F. et al., J. Mol. Biol., 215, 403-410, 1990). The homology in the amino acid sequence may be calculated by a BLAST search algorithm. More particularly, it may be calculated using a bl2seq program (Tatiana A. Tatusova and Thomas L. Madden, FEMS Microbiol. Lett., 174, 247-250, 1999) in a BLAST package (sgi32 bit edition, version 2.0.12; obtained from NCBI) in accordance with a default parameter. As a pairwise alignment parameter, a program "blastp" is used. Further, "0" as a Gap insertion cost value, "0" as a Gap elongation cost value, "SEG" as a filter for a Query sequence, and "BLOSUM62" as a Matrix are used, respectively.

The present invention includes "a polypeptide exhibiting an activity of inhibiting glucose uptake into an adipocyte by an insulin stimulation, and consisting of a partial fragment of the polypeptide consisting of the amino acid sequence of SEQ ID NO: 2 or SEQ ID NO: 14".

(2) Cell-type Screening Tool

The cell which may be used as the cell-type screening tool of the present invention (hereinafter referred to as a cell for a screening tool) is not particularly limited, so long as it expresses the polypeptide for a screening tool when using as the cell-type screening tool. The cell for a screening tool may be a transformant in which the polypeptide for a screening tool is artificially expressed, or a naturally occurring cell which is known to express the polypeptide for a screening tool, or a cell strain thereof. A transformant obtained by transformation with the polypeptide for a screening tool is preferable. As a most preferred cell-type screening tool, there may be mentioned, for example, (i) a transformant expressing the polypeptide consisting of the amino acid sequence of SEQ ID NO: 2 or SEQ ID NO: 14;

(ii) a transformant expressing the variation functionally equivalent; and (iii) a transformant expressing the homologous polypeptide.

(3) Promoter-type Screening Tool

The polypeptide which may be used as the promoter-type screening tool of the present invention (hereinafter referred to as a promoter of the present invention) is not particularly limited, so long as it is (1) a polynucleotide consisting of the base sequence consisting of the 34th to 2014th bases in the base sequence of SEQ ID NO: 20, (2) a polynucleotide exhibiting a promoter activity of the polypeptide for a screening tool, and comprising a base sequence in which one or more bases are substituted, deleted, and/or inserted at 1 to 10 positions in the base sequence consisting of the 34th to 2014th bases-in the base sequence of SEQ ID NO: 20, (3) a polynucleotide exhibiting a promoter activity of the polypeptide for a screening tool, and comprising at least a part of the base sequence consisting of the 34th to 2014th bases in the base sequence of SEQ ID NO: 20, or (4) a polynucleotide exhibiting a promoter activity of the polypeptide for a screening tool, and hybridizing under stringent conditions to a polynucleotide consisting of the base sequence consisting of the 34th to 2014th bases in the base sequence of SEQ ID NO: 20. As the promoter of the present invention, for example, (i) a polynucleotide consisting of the base sequence consisting of the 34th to 2014th bases in the base sequence of SEQ ID NO: 20;

(ii) a polynucleotide exhibiting a promoter activity of the polypeptide for a screening tool, and comprising a polynucleotide consisting of the 34th to 2014th bases in the base sequence of SEQ ID NO: 20, or (iii) a polynucleotide exhibiting a promoter activity of the polypeptide for a screening tool, and comprising a base sequence in which one or more (preferably 1 to 10 in total, more preferably 1 to 5, most preferably 1 to 3) bases are substituted, deleted, and/or inserted at 1 to 10 positions in the base sequence consisting of the 34th to 2014th bases in the-base sequence of SEQ ID NO: 20 is preferable, and a polynucleotide exhibiting a promoter activity of the polypeptide of the present invention described below is more preferable.

The term "stringent conditions" as used herein means conditions in which non-specific hybridization does not occur, more particularly, conditions in which a 0.1×SSC (Saline-sodium citrate buffer) solution containing 0.1% sodium dodecyl sulfate (SDS) is used and the temperature is 65° C.

The cell which may be used as the promoter-type screening tool of the present invention (hereinafter referred to as a cell expressing a promoter of the present invention) is not particularly limited, so long as it is a cell expressing a promoter activity. As the cell expressing a promoter of the present invention, a cell transformed with the promoter of the present invention is preferable.

The term "promoter activity" as used herein means an activity of regulating an amount of an mRNA transcribed from a gene located downstream of the promoter. "To exhibit a promoter activity of the polypeptide for a screening tool (or polypeptide of the present invention)" as used herein means to be able to confirm a promoter activity of the polypeptide for a screening tool (or polypeptide of the present invention) by the method described in Example 12.

A substance which inhibits an expression of the polypeptide for a screening tool of the present invention or the polypeptide of the present invention can be screened, by using the promoter of the present invention and analyzing whether or not a substance to be tested inhibit an activity of the promoter of the present invention. The polypeptide for a screening tool of the present invention or the polypeptide of the present invention inhibits glucose uptake by insulin. Therefore, a substance which inhibits the promoter activity, i.e., a substance which inhibits the polypeptide expression, alleviates the inhibition of glucose uptake by insulin (i.e., insulin resistance), and is useful as an active ingredient of a therapeutic agent for treating diabetes (particularly an agent for alleviating insulin resistance). The promoter-type screening tool of the present invention may be used as a screening tool for a therapeutic agent for treating diabetes (particularly an agent for alleviating insulin resistance).

2. Polypeptide and Polynucleotide of the Present Invention

The polypeptide of the present invention includes the polypeptide consisting of the amino acid sequence of SEQ ID NO: 2, or the polypeptide exhibiting an activity of inhibiting glucose uptake into an adipocyte by an insulin stimulation, and comprising the amino acid sequence of SEQ ID NO: 2.

The polynucleotide of the present invention is not particularly limited, so long as it encodes the polypeptide of the present invention. As the polynucleotide of the present invention, a polynucleotide which encodes "the polypeptide consisting of the amino acid sequence of SEQ ID NO: 2", more particularly a polynucleotide consisting of the base sequence consisting of the 1st to 2472nd bases in the base sequence of SEQ ID NO: 1, is preferable. In this connection, the term "polynucleotide" as used herein includes both DNA and RNA.

3. Method for Producing the Polypeptide-type or Cell-type Screening Tool, Polypeptide, and Polynucleotide of the Present Invention The method for producing the polynucleotide of the present invention and the polynucleotide which encodes the polypeptide for a screening tool (hereinafter referred to as a polynucleotide for a screening tool) is not particularly limited. As the process, there may be mentioned, for example, (a) a method utilizing a polymerase chain reaction (PCR), (b) a method utilizing conventional genetic engineering techniques (i.e., a method for selecting a transformant containing the desired cDNA from strains transformed with a cDNA library), (c) a chemical synthesis method, or the like. These methods will be explained in this order hereinafter.

In the method using PCR [the above method (a)], the polynucleotide of the present invention or the polynucleotide for a screening tool may be produced, for example, by the following procedure.

mRNA is extracted from cells (for example, human or mouse cells) or tissue capable of producing the polypeptide of the present invention or the polypeptide for a screening tool. A primer set consisting of a pair of primers, between which full-length mRNA corresponding to the polypeptide or a partial region of the mRNA is located, is synthesized on the basis of the base sequence of a polynucleotide encoding the polynucleotide. Full-length cDNA encoding the polypeptide of the present invention or the polypeptide for a screening tool, or a part of the full-length cDNA may be obtained, by adjusting reaction conditions (for example, denaturation temperature, conditions for adding a denaturing agent, or the like) and performing a reverse transcriptase-polymerase chain reaction (RT-PCR).

Alternatively, full-length cDNA encoding the polypeptide or a part of the cDNA may be obtained, by performing PCR using, as a template, cDNA prepared using reverse transcriptase and mRNA derived from cells (for example, human or mouse cells) or tissue capable of producing the polypeptide, or commercially available cDNA derived from human or mouse cells or tissue.

The polypeptide may be manufactured by inserting the resulting full-length cDNA or a part thereof into an appropriate expression vector and expressing it in host cells.

In the method using conventional genetic engineering techniques [the above method (b)], the polynucleotide of the present invention or the polynucleotide for a screening tool may be produced, for example, by the following procedure.

First, single-stranded cDNA is synthesized by using reverse transcriptase from mRNA prepared by the above-mentioned PCR method as a template, and then double-stranded cDNA is synthesized from the single-stranded cDNA. Next, a recombinant plasmid comprising the double-stranded cDNA is prepared and introduced into *Escherichia coli*, such as a DH5α strain, HB101 strain, or JM109 strain, thereby transforming the strain. A transformant is selected using a drug resistance against, for example, tetracycline, ampicillin, or kanamycin as a marker.

As a method for selecting a transformant containing the desired cDNA from the resulting transformants, for example, (1) a screening method utilizing hybridization with a synthetic oligonucleotide probe, or (2) a screening method utilizing hybridization with a probe prepared by PCR, may be used.

The polynucleotide of the present invention or the polynucleotide for a screening tool may be obtained from the resulting transformant of interest in accordance with known methods, for example, by separating a fraction corresponding to plasmid DNA from the cells and cutting out the cDNA region from the plasmid DNA.

In the method using a chemical synthesis method [the above method (c)], the polynucleotide of the present invention or the polynucleotide for a-screening tool may be produced, for example, by binding DNA fragments produced by a chemical synthesis method. Each DNA can be synthesized using a DNA synthesizer [for example, Oligo 1000M DNA Synthesizer (Beckman) or 394 DNA/RNA Synthesizer (Applied Biosystems)].

Those skilled in the art may prepare a polynucleotide encoding a polypeptide having an activity similar to a naturally-occurring activity inhibiting glucose uptake into an adipocyte by an insulin stimulation, by performing modifications, such as substitution, deletion, and/or addition, in a part of a naturally-occurring base sequence. A polynucleotide encoding the variation functionally equivalent or homologous polypeptide having an inhibitory activity the same as that of a naturally-occurring polypeptide may be prepared by, for example, an introduction of deletion by a restriction enzyme and/or DNA exonuclease, an introduction of variations by site-specific mutagenesis [Nucleic Acid Res. 10, 6487 (1982)], a direct introduction of a synthetic mutant DNA [Maniatis, T. et al. (1989) "Molecular Cloning—A Laboratory Manual $2^{nd}$ Edt." Cold Spring Harbor Laboratory, NY], or the like.

Determination of the DNA sequences obtained by the above-mentioned methods can be carried out by, for example, a Maxam-Gilbert chemical modification method (Maxam, A. M. and Gilbert, W., "Methods in Enzymology", 65, 499-559, 1980) or a dideoxynucleotide chain termination method (Messing, J. and Vieira, J., Gene, 19, 269-276, 1982).

An isolated polynucleotide of the present invention or polynucleotide for a screening tool is re-integrated into an appropriate vector DNA and a host cell (including a eucaryotic host cell and a procaryotic host cell) may be transformed by the resulting expression vector. Further, it is possible to express the polynucleotide in a desired host cell, by introducing an appropriate promoter and a sequence related to the gene expression into the vector.

In the eucaryotic host cells, for example, cells of vertebrates, insects, and yeast are included. As the vertebral cell, there may be mentioned, for example, a simian COS cell (Gluzman, Y., Cell, 23, 175-182, 1981), a dihydrofolate reductase defective strain of a Chinese hamster ovary cell (CHO) (Urlaub, G. and Chasin, L. A., Proc. Natl. Acad. Sci. USA, 77, 4216-4220, 1980), a human fetal kidney derived HEK293 cell, or a 293-EBNA cell (Invitrogen) obtained by introducing an EBNA-1 gene of Epstein Barr Virus into HEK293 cell.

As an expression vector for a vertebral cell, a vector containing a promoter positioned upstream of the polynucleotide to be expressed, an RNA splicing site, a polyadenylation site, a transcription termination sequence, and the like may be generally used. The vector may further contain a replication origin, if necessary. As the expression vector, there may be mentioned, for example, pSV2dhfr containing an SV40 early promoter (Subramani, S. et al., Mol. Cell. Biol., 1, 854-864, 1981), pEF-BOS containing a human elongation factor promoter (Mizushima, S. and Nagata, S., Nucleic Acids Res., 18,5322, 1990), or pCEP4 containing a cytomegalovirus promoter (Invitrogen).

When the COS cell is used as the host cell, a vector which has an SV40 replication origin, can perform an autonomous replication in the COS cell, and has a transcription promoter, a transcription termination signal, and an RNA splicing site, may be used as the expression vector. As the vector, there may be mentioned, for example, pME18S (Maruyama, K. and Takebe, Y., Med. Immunol., 20, 27-32, 1990), pEF-BOS (Mizushima, S. and Nagata, S., Nucleic Acids Res., 18, 5322, 1990), or pCDM8 (Seed, B., Nature, 329, 840-842, 1987).

The expression vector may be incorporated into COS cells by, for example, a method using a commercially available transfection reagent (for example, FuGENE™6 Transfection Reagent; Roche Diagnostics).

When the CHO cell is used as the host cell, a transformant capable of stably producing the polypeptide of the present invention or the polynucleotide for a screening tool can be obtained by carrying out a co-transfection of an expression vector comprising the polynucleotide of the present invention or the polynucleotide for a screening tool, together with a vector capable of expressing a neo gene which functions as a G418 resistance marker, such as pRSVneo (Sambrook, J. et al., "Molecular Cloning-A Laboratory Manual", Cold Spring Harbor Laboratory, NY, 1989) or pSV2-neo (Southern, P. J. and Berg, P., J. Mol. Appl. Genet., 1, 327-341, 1982), and selecting a G418 resistant colony.

When the 293-EBNA cell is used as the host cell, for example, pCEP4 (Invitrogen) containing a replication origin of Epstein Barr Virus and capable of performing an autonomous replication in the 293-EBNA cell may be used as the expression vector.

The transformant may be cultured in accordance with the conventional method, and the polypeptide of the present invention or the polynucleotide for a screening tool is transmembranously produced. As a medium to be used in the culturing, a medium commonly used in a desired host cell may be appropriately selected. In the case of the COS cell, for example, a medium such as an RPMI-1640 medium or a Dulbecco's modified Eagle's minimum essential medium (DMEM) may be used, by supplementing it with a serum component such as fetal bovine serum (FBS) if necessary. In the case of the 293-EBNA cell, a medium such as a Dulbecco's modified Eagle's minimum essential medium (DMEM) with a serum component such as fetal bovine serum (FBS) and G418 may be used.

The polypeptide of the present invention or the polynucleotide for a screening tool produced by culturing the transformants of the present invention may be separated and purified therefrom by various known separation techniques making use of the physical properties, chemical properties and the like of the polypeptide. More particularly, the above polypeptide may be purified by treating the cells or cell membrane fraction containing the polypeptide with a commonly used treatment, for example, a treatment with a protein precipitant, ultrafiltration, various liquid chromatography techniques such as molecular sieve chromatography (gel filtration), adsorption chromatography, ion exchange chromatography, affinity chromatography, or high performance liquid chromatography (HPLC), or dialysis, or a combination thereof.

When the polypeptide of the present invention or the polynucleotide for a screening tool is expressed as a fusion protein with a marker sequence in frame, identification of the expression of the polypeptide, purification thereof, or the like may be easily carried out. As the marker sequence, there may be mentioned, for example, a FLAG epitope, a hexahistidine tag, a hemagglutinin tag, or a myc epitope. Further, by inserting a specific amino acid sequence recognized by a protease such as enterokinase, factor Xa, or thrombin between the marker sequence and the polypeptide, the marker sequence may be removed by the protease.

4. Method for Producing the Promoter and the Cell Expressing the Promoter of the Present Invention The promoter of the present invention may be prepared by the following methods, as well as by the method described in Example 11.

(1) Preparation Using the PCR Method

As described in Example 11, PCR is carried out using primers and human genomic DNA to prepare a DNA comprising the base sequence consisting of the 34th to 2014th bases in the base sequence of SEQ ID NO: 20. Generally, allele variations are well-known. When DNAs are prepared by the above method, a polynucleotide exhibiting the promoter activity of the polypeptide for a screening tool of the present invention and comprising a base sequence in which one or more bases are substituted, deleted, and/or inserted at any position in the base sequence consisting of the 34th to 2014th bases in the base sequence of SEQ ID NO: 20, may be sometimes obtained. Such a polynucleotide is also included in the promoter of the present invention as described above.

(2) Preparation Using DNA Synthesis

The polynucleotide may be prepared by chemically synthesizing and binding DNA fragments which are divided from the base sequence consisting of the 34th to 2014th bases in the base sequence of SEQ ID NO: 20 and the chain complementary thereto. The DNA fragments can be synthesized by a DNA synthesizer.

It may be confirmed whether or not the obtained polynucleotide exhibits the promoter activity of the polypeptide for a screening tool of the present invention (or the polypeptide of the present invention) by, for example, the method described in Example 12.

Those skilled in the art may prepare a polynucleotide having a promoter activity similar to that of a naturally-occurring promoter, by performing modifications, such as substitution, deletion, and/or addition, in a part of the base sequence of a naturally-occurring promoter sequence. A polynucleotide having a base sequence in which one or more bases are substituted, deleted, and/or added in a naturally-occurring base sequence and having a promoter activity similar to that of a naturally-occurring promoter, is included in the promoter of the present invention as described above. The base modifications may be carried out by, for example, an introduction of deletion by a restriction enzyme and/or DNA exonuclease, an introduction of variations by site-specific mutagenesis, a modification of a promoter sequence by the PCR method using mutant primers, a direct introduction of a synthetic mutant DNA, or the like.

The cell expressing the promoter of the present invention may be prepared by incorporating the promoter of the present invention into a host cell appropriately selected in accordance with the object. It is preferable to prepare the cell by incorporating the promoter of the present invention into a vector appropriately selected in accordance with the object. For example, when a system for analyzing the inhibition of a promoter activity is constructed, it is preferable to prepare the cell by incorporating the promoter of the present invention into a vector having a reporter gene such as luciferase, as described in Examples 11 and 12. For example, when a system for screening a substance capable of controlling the activity of the promoter of the present-invention, preferably a cell derived from a mammal such as human, mouse, rat, or the like, more preferably a cell derived from a human, may be used.

5. Analysis Method and Screening Method of the Present Invention (1) Method Using the Polypeptide for a Screening Tool or the Cell for a Screening Tool An analysis whether or not a substance to be tested inhibits the activity of the polypeptide for a screening tool and a screening of an inhibitor therefor may be carried out, by utilizing the activity of inhibiting glucose uptake into an adipocyte by an insulin stimulation. The inhibitor for the polypeptide is useful as an active ingredient of an agent for treating or preventing diabetes (preferably type II diabetes, particularly insulin resistance), and thus it is possible to screen a therapeutic agent for diabetes (preferably type II diabetes, particularly insulin resistance).

The method of the present invention for analyzing whether or not a substance to be tested is an inhibitor of the polypeptide for a screening tool comprises the steps of: bringing a cell expressing the polypeptide for a screening tool into contact with the substance to be tested, and analyzing an amount of glucose uptake by an insulin stimulation. The method for screening an inhibitor of the polypeptide for a screening tool or a therapeutic agent for diabetes comprises the steps of:

analyzing a substance to be tested by the above method, and selecting an inhibitor.

More particularly, for example, adipocytes, or cells (such as 3T3-L1 cells) obtained by-differentiating cells other than the adipocyte into adipocytes may be used as the cells expressing the polypeptide for a screening tool. It is preferable to use the cells which are differentiated from the 3T3-L1 cells into adipocytes and express the polypeptide of SEQ ID NO: 2 or SEQ ID NO: 14, used in Example 7 (Ezaki et al., "IGAKU NO AYUMI (Journal of Clinical and Experimental Medicine", 503-506, 1998).

An amount of glucose uptake can be analyzed (detected or measured) in accordance with a conventional method. The method described in Example 7 is preferable as the analysis method. More particularly, an amount of glucose uptake when bringing the test substance into contact with the cells expressing the polypeptide, and an amount of glucose uptake without the contact are measured, respectively. It can be judged that a test substance in which the amount of glucose uptake when the test substance is brought into contact with the cells is increased in comparison with that without the contact is the inhibitor of the polypeptide, and thus is useful as an active ingredient of an agent for treating or preventing diabetes (preferably type II diabetes, particularly insulin resistance).

When an inhibitor of the polypeptide for a screening tool is selected by the screening method of the present invention, a degree of increase in the amount of glucose uptake is preferably 20% or more, more preferably 50% or more, most preferably 80% or more.

(2) Method Using the Promoter-type Screening Tool of the Present Invention

The analysis method of the present invention includes the method for analyzing whether or not a substance to be tested-inhibits an activity of the promoter of the present invention, comprising the steps of:

bringing the cell expressing the promoter of the present invention (preferably the cell transformed with the expression vector containing the promoter of the present invention) into contact with the substance to be tested, and analyzing (detecting or measuring) the promoter activity.

As the method for analyzing the promote activity, a method using a reporter gene plasmid comprising the base sequence consisting the 34th to 2014th bases in the base sequence of SEQ ID NO: 20 described in Example 12 is convenient. The reporter gene is a gene encoding a protein which can be quantified by a conventional method (known quantifying methods such as measurement of an enzyme activity or the like). As the reporter gene, for example, each gene of chloramphenicol acetyl transferase, luciferase, β-galactosidase, or alkaline phosphatase is often used, but is not limited. The original vector for constructing the reporter gene plasmid is not limited, but commercially available plasmid vectors, such as pGV-B2 (Toyo Ink MFG) or pSEAP2-Basic (Clontech), may be used. The existence and/or strength of the promoter activity of the sequence can be determined by constructing the reporter gene plasmid in which the sequence is incorporated in the forward direction upstream of the reporter gene in the vector, and then measuring an amount of the reporter protein expressed in the cells transformed with the plasmid in accordance with an appropriate method. Further, an action of a test substance with respect to the promoter activity can be analyzed by adding the test substance to culture medium of the transformant.

The present invention includes a method for screening a substance which inhibits an expression of the polypeptide for a screening tool of the present invention (preferably the polypeptide of the present invention), or a method for screening a therapeutic agent for diabetes (particularly an agent for alleviating insulin resistance), comprising the steps of:

analyzing a substance to be tested described above, and selecting a substance which inhibits the promoter activity.

As the substance which inhibits the promoter activity selected by the screening method, a substance which inhibits it by 20% or more in accordance with the method described in Example 12 is preferable, a substance which inhibits it by 50% or more is more preferable, and a substance which inhibits it by 80% or more is most preferable;

Compounds to be tested which may be applied to the screening method of the present invention are not particularly limited, but there may be mentioned, for example, various known compounds (including peptides, or antibodies or fragments thereof) registered in chemical files, commercially available compounds, compounds obtained by combinatorial chemistry techniques (Terrett, N. K. et al., Tetrahedron, 51, 8135-8137, 1995) or conventional synthesis techniques, random peptides prepared by employing a phage display method (Felici, F. et al., J. Mol. Biol., 222, 301-310, 1991), culture supernatants of microorganisms, natural components derived from plants or marine organisms, animal tissue extracts, or the like. Further, compounds (including peptides, or antibodies or fragments thereof) obtained by chemically or biologically modifying compounds (including peptides) selected by the screening method of the present invention may be used.

6. Process for Manufacturing the Pharmaceutical Composition for Treating Diabetes of the Present Invention The process for manufacturing the pharmaceutical composition for treating diabetes (including pharmaceutical composition for treating and preventing diabetes) of the present invention comprises the steps of:

(i) (a) analyzing an inhibitor using the cell for a screening tool of the present invention or (b) analyzing a promoter activity using the promoter-type screening tool of the present invention, as described above, and (II) preparing a medicament containing the substance.

The process for manufacturing a pharmaceutical composition for treating diabetes of the present invention includes a process for manufacturing a pharmaceutical composition for treating diabetes comprising the steps of:

analyzing, in a quality control test of a pharmaceutical composition for treating diabetes, whether or not the pharmaceutical composition inhibits the activity of inhibiting glucose uptake by an insulin stimulation or the promoter activity, by the analysis method of the present invention, and preparing a medicament.

The present invention includes a pharmaceutical composition for treating diabetes comprising as an active ingredient a substance which inhibits the activity of inhibiting glucose uptake by an insulin stimulation or the promoter activity, selected by the screening method of the present invention. The process of the present invention for manufacturing a pharmaceutical composition for treating diabetes includes a process for manufacturing a pharmaceutical composition for treating diabetes comprising the step of preparing a medicament containing the substance selected by the screening method of the present invention comprising the above-described analysis step of the present invention.

A DNA comprising at least a part of the base sequence of SEQ ID NO: 20 can competitively inhibit the binding between the promoter of the present invention and a protein (for example, a transcription factor) capable of binding thereto, independently of having the promoter activity. Therefore, when the above DNA corresponds to the binding site of a protein capable of promoting the activity of the promoter of the present invention, the promoter activity can be inhibited by administering the DNA. The DNA used for the competitive inhibition has generally a length of at least of 6 bases or more, preferably 10 bases or more.

The pharmaceutical composition of the present invention may be prepared using carriers, fillers, and/or other additives generally used in the preparation of medicaments, in accordance with the active ingredient.

Examples of administration include oral administration by tablets, pills, capsules, granules, fine granules, powders, oral solutions and the like, and parenteral administration by injections (e.g., intravenous, intramuscular, or the like), suppositories, transdermal preparations, transmucosal absorption preparations and the like. Particularly, in the case of peptides which are digested in the stomach, a parenteral administration such as an intravenous injection or the like, or preparation techniques in which the polypeptide is not digested, such as a preparation technique disclosed in the WO95/28963 pamphlet, is preferable.

In the solid composition for use in the oral administration, one or more active substances may be mixed with at least one inert diluent such as lactose, mannitol, glucose, microcrystalline cellulose, hydroxypropylcellulose, starch, polyvinyl pyrrolidone, or aluminum magnesium silicate. In the usual way, the composition may contain additives other than the inert diluent, such as a lubricant, a disintegrating agent, a stabilizing agent, or a solubilizing or solubilization assisting agent. If necessary, tablets or pills may be coated with a sugar coating or a film of a gastric or enteric substance.

The liquid composition for oral administration may include, for example, emulsions, solutions, suspensions, syrups, and elixirs, and may contain a generally used inert diluent such as purified water or ethyl alcohol. The composition may contain additives other than the inert diluent, such as moistening agents, suspending agents, sweeteners, flavors, or antiseptics.

The injections for parenteral administration may include aseptic aqueous or non-aqueous solutions, suspensions, and emulsions. Examples of the diluent for use in the aqueous solutions and suspensions include distilled water for injection use and physiological saline. Examples of the diluent for use in the non-aqueous solutions and suspensions include propylene glycol, polyethylene glycol, plant oil (e.g., olive oil), alcohols (e.g., ethanol), polysorbate 80 and the like. Such a composition may further contain a moistening agent, an emulsifying agent, a dispersing agent, a stabilizing agent, a solubilizing or solubilization assisting agent, an antiseptic or the like. These compositions may be sterilized, for example, by filtration through a bacteria retaining filter, blending of a germicide, or irradiation. Alternatively, they may be used by first making them into sterile solid compositions and dissolving them in sterile water or other sterile solvent for injection use prior to their use.

The dose is optionally decided by taking into consideration the strength of each active ingredient selected by the aforementioned screening method, or symptoms, age, sex, or the like of each patient to be administered.

For example, in the case of oral administration, the usual dosage for an adult (60 kg in weight) is about 0.01 to 1000 mg, preferably 0.01 to 100 mg per day. In the case of parenteral administration, the usual dosage is about 0.01 to 1000 mg, preferably 0.01 to 100 mg per day in the form of an injection.

7. Probe of the Present Invention

The present invention includes a probe which hybridizes to the polynucleotide of the present invention under stringent conditions.

The term "stringent conditions" as used herein means the conditions as described above.

The probe of the present invention may be used for examining an amount of expression of the polynucleotide encoding the polypeptide of the present invention (particularly the polypeptide consisting of the amino acid sequence of SEQ ID NO: 2). Diabetes can be diagnosed by the increased amount of the expression (preferably expression in adipocytes) as an indicator.

As described above, the present invention includes a method for detecting diabetes using the probe of the present invention. According to the detection method of the present invention, diabetes can be detected by bringing the probe of the present invention into contact with a sample to be tested, and then analyzing a complex of the polynucleotide (such as mRNA, or cDNA derived therefrom) encoding the polypeptide (particularly the polypeptide consisting of the amino acid sequence of SEQ ID NO: 2) of the present invention and the probe by a known analysis method (such as northern blotting). Further, the probe of the present invention can be applied to a gene chip to analyze an amount of expression. When the amount of the complex, i.e, the amount of the polynucleotide encoding the polypeptide of the present invention, is increased in comparison with that of a healthy person, it can be judged that the patient suffers from diabetes.

EXAMPLES

The present invention now will be further illustrated by, but is by no means limited to, the following Examples. The procedures were performed in accordance with known methods described in laboratory manuals for genetic engineering (for example, Sambrook, J. et al., "Molecular Cloning-A Laboratory Manual", Cold Spring Harbor Laboratory, NY, 1989), unless otherwise specified.

Example 1

Cloning of Human MD8 Gene and Construction of Expression Vectors (1) Cloning of Human MD8 cDNA A polymerase chain reaction (PCR) was performed to obtain a human ortholog gene corresponding to the gene of GenBank Accession No. X13335. In the PCR, human placenta cDNA (Marathon-Ready™ cDNA; Clontech) was used as a template, oligo DNA consisting of the base sequence of SEQ ID NO: 6 and oligo DNA consisting of the base sequence of SEQ ID NO: 7 were used as primers, and LAtaqDNA polymerase (Takara Shuzo) was used. The PCR was carried out by performing a reaction at 94° C. for 2 minutes and then repeating a cycle consisting of reactions at 98° C. for 20 seconds and at 68° C. for 2 minutes and 30 seconds 40 times. A DNA fragment of approximately 2.5 kbp was separated and extracted as a template solution A by an agarose electrophoresis.

PCR was performed by using the resulting template solution A as a template to obtain a DNA fragment A of approximately 2.0 kbp. In the PCR, oligo DNA consisting of the base sequence of SEQ ID NO: 8 (having the restriction enzyme XbaI recognition sequence added to the base sequence consisting of the 1st to 18th bases in the base sequence of SEQ ID NO: 1) and oligo DNA consisting of the base sequence of SEQ ID NO: 9 (having the restriction enzyme BamHI recognition sequence added to the base sequence complementary to that consisting of the 1918th to 1938th bases in the base sequence of SEQ ID NO: 1) were used as primers, and DNA polymerase (Pyrobest DNA polymerase; Takara Shuzo) was used. The PCR was carried out by performing a reaction at 94° C. for 2 minutes, repeating a cycle consisting of reactions at 98° C. for 20 seconds, at 60° C. for 30 seconds, and at 72° C. for 2 minutes and 30 seconds 15 times, and performing a reaction at 72° C. for 7 minutes.

Similarly, PCR was performed by using the template solution A as a template to obtain a DNA fragment B of approximately 0.7 kbp. In the PCR, oligo DNA consisting of the base sequence of SEQ ID NO: 10 (base sequence consisting of the 1795th to 1824th bases in the base sequence of SEQ ID NO: 1) and oligo DNA consisting of the base sequence of SEQ ID NO: 11 (having the restriction enzyme BamHI recognition sequence added to the base sequence complementary to that consisting of the 2443rd to 2472nd bases-in the base sequence of SEQ ID NO: 1) were used as primers, and DNA polymerase (Pyrobest DNA polymerase; Takara Shuzo) was used. The PCR was carried out by performing a reaction at 94° C. for 2 minutes, repeating a cycle consisting of reactions at 98° C. for 20 seconds, at 60° C. for 30 seconds, and at 72° C. for 1 minute 15 times, and performing a reaction at 72° C. for 7 minutes.

The resulting DNA fragments A and B were independently subcloned at the EcoRV site of plasmid pZErO2.1 (Invitrogen). The base sequences of the resulting plasmids (designated pzErO-MD8A and pZErO-MD8B, respectively) was analyzed using a DNA sequencer (ABI3700 DNA Sequencer; Applied Biosystems) by a dideoxy terminator method to obtain an ORF consisting of the base sequence of SEQ ID NO: 1. As a result, neither the base sequence of SEQ ID NO: 1 nor the amino acid sequence of SEQ ID NO: 2 deduced from the base sequence was found in the registered sequences of GenBank and SwissProt, and it was found that those of SEQ ID NOS: 1 and 2 are novel. In this connection, as a known base sequence in which a base is different from that of SEQ ID NO: 1 and a known amino acid sequence in which an amino acid is different from that of SEQ ID NO: 2, the base sequence of GenBank Accession No. D26579 and the amino acid sequence of SwissProt Accession No. BAA05626 exist, respectively. The known sequence is designated as "ADAM8", but the relationship between ADAM8 and diabetes is not known.

Hereinafter, the protein encoded by the ORF (i.e., polypeptide consisting of the amino acid sequence consisting of the 1st to 824th amino acids in the amino acid sequence of SEQ ID NO: 2) is referred to as "human MD8".

(2) Construction of Vector for Expressing Human MD8 Full-length Protein (MD8)

A DNA fragment of approximately 1.8 kbp generated by digesting the plasmid pZErO-MD8A obtained in Example 1(1) with restriction enzymes XbaI and BstYI, and a DNA fragment of approximately 0.6 kbp generated by digesting the plasmid pZErO-MD8A obtained in Example 1(1) with restriction enzymes BstYI and BamHI were inserted between the XbaI site and BamHI site of plasmid pCEPdE2-FLAG (Example 7-1 in WO01/34785) to construct a plasmid pCEPdE2-MD8-FLAG for expressing a protein MD8-FLAG in which a FLAG tag of SEQ ID NO: 12 was added to the C-terminus of the MD8 protein.

(3) Construction of Vector for Expressing MD8 Extracellular Protein (MD8s)

A DNA fragment of approximately 2.0 kbp generated by digesting the plasmid pZErO-MD8A obtained in Example 1(1) with restriction enzymes XbaI and BamHI was inserted between the XbaI site and BamHI site of plasmid pCEPdE2-FLAG to construct a plasmid pCEPdE2-MD8S-FLAG for expressing a protein MD8S-FLAG in which a FLAG tag of SEQ ID NO: 12 was added to the C-terminus of the amino acid sequence consisting of the 1st to 646th amino acids, corresponding to an extracellular region of the MD8 protein (hereinafter referred to as MD8S), in the amino acid sequence of SEQ ID NO: 2.

Example 2

Expression of MD8S Protein and MD8 Protein in Animal Cell Strain

The expression plasmid pCEPdE2-MD8S-FLAG prepared in Example 1(3) was introduced into HEK293-EBNA cells (Invitrogen) with a transfection reagent (FuGENE™6 Transfection Reagent; Boeringer Mannheim) in accordance with a manual attached to the reagent to express the MD8S protein. After the introduction of the plasmid, it was confirmed by western blotting using an antibody-against the FLAG tag added to the C-terminus (mouse anti-FLAG monoclonal antibody M2; Sigma) that the protein of interest (i.e., MD8S-FLAG protein) was contained in a culture supernatant obtained by culturing for 2 days.

More particularly, the culture supernatant was electrophoresed using an SDS/4%-20% acrylamide gel (Daiichi Pure Chemicals) and transferred onto a polyvinylidene difluoride (PVDF) membrane using a blotting apparatus. After the transfer, the PVDF membrane was blocked by adding a blocking reagent (Block Ace; Dainippon pharmaceutical), and reacted with the mouse anti-FLAG monoclonal antibody M2, followed by a horseradish peroxidase-labeled rabbit anti-mouse IgG polyclonal antibody (Zymed or TAGO). Alternatively, after blocking, the membrane was reacted with a biotinylated M2 antibody (Sigma), followed by a horseradish peroxidase-labeled streptavidin (Amersham). After the reaction, the expression of the protein of interest was confirmed using an ECL western blotting detection system (Amersham Pharmacia). The expressed proteins were detected as two bands. One molecular weight was approximately 90 kDa, which was identical to the value calculated from the amino acid sequence thereof, and the other was approximately 67 kDa, which was approximately 23 kDa smaller.

Similarly, the MD8 protein was expressed by using the expression plasmid pCEPdE2-MD8-FLAG prepared in Example 1(2). In this connection, since the MD8 protein contains a transmembrane region, the expression was confirmed by western blotting a cell fraction after 2 days from the plasmid introduction and detecting a 100 kDa band.

Example 3

Cloning of Mouse MD8 Gene

PCR was performed to obtain a gene of which the expression was increased in a diabetes model as shown in Referential Example described below, by using mouse 11-day embryo cDNA and mouse 17-day embryo cDNA (Marathon-Ready cDNA; Clontech) as a template, DNA consisting of the base sequence of SEQ ID NO: 16 as a 5' primer, DNA consisting of the base sequence of SEQ ID NO: 17 as a 3' primer, and LAtaqDNA polymerase (Takara Shuzo). The PCR was carried out by performing a reaction at 94° C. for 2 minutes and then repeating a cycle consisting of reactions at 98° C. for 10 seconds, at 60° C. for 30 seconds, and at 68° C. for 2 minutes and 30 seconds 40 times. The resulting DNA fragments of approximately 3.6 kbp and approximately 2.5 kbp were separated and extracted by an agarose electrophoresis. The base sequences of the fragments were analyzed using a DNA sequencer (ABI3700 DNA Sequencer; Applied Biosystems) by a dideoxy terminator method to determine an ORF consisting of the base sequence of SEQ ID NO: 13.

As a result, the base sequence of the DNA fragment (approximately 3.6 kbp) generated from the 11-day embryo accorded with that of the DNA fragment (approximately 2.5 kbp) generated from the 17-day embryo, except that the approximately 3.6 kbp fragment from the 11-day embryo contained an insertion of approximately 1.0 kbp which did not exist in the approximately 2.5 kbp fragment from the 17-day embryo and the X13335 gene. Further, it was found that the base sequence of the approximately 2.5 kbp fragment was different at three positions (two positions with respect to the deduced amino acid sequence) from that of X13335. The approximately 2.5 kbp DNA fragment generated from the 17-day embryo was subcloned into pCR2.1 (Invitrogen) to obtain pCR-mMD8L.

Example 4

Construction of Adenovirus Vector for Expressing MD8 and Preparation of Adenovirus Solution (1) Construction of Adenovirus Vector for Expressing Mouse MD8 and Preparation of Adenovirus Solution PCR was performed by using pCR-mMD8L as a template, DNA consisting of the base sequence of SEQ ID NO: 18 as a 5' primer, DNA consisting of the base sequence of SEQ ID NO: 19 as a 3' primer, and DNA polymerase (Pyrobest DNA polymerase; Takara Shuzo). The PCR was carried out by performing a reaction at 94° C. for 2 minutes, repeating a cycle consisting of reactions at 98° C. for 20 seconds, at 55° C. for 30 seconds, and at 72° C. for 3 minutes 15 times, and performing a reaction at 72° C. for 7 minutes. The resulting DNA fragment of approximately 2.5 kbp was inserted at the EcoRV site of plasmid pZErO2.1 (Invitrogen) to construct pZErO-mMD8L. The plasmid was digested with a restriction enzyme XbaI, and then the resulting DNA fragment of approximately 2.5 kbp was inserted into and ligated with a pAdTrack-CMV vector (He T. C. et al., Proc. Natl. Acad. Sci. USA., 95, 2509-2514, 1998), which had been previously digested with a restriction enzyme XbaI and dephosphorylated with alkaline phosphatase (BAPC75; Takara Shuzo). Among the clones, a clone in which the ORF of mMD8 was located in the direction similar to the CMV promoter was selected to designated pAdTrack-CMV-mMD8. Thereafter, an adenovirus solution having a high titer and expressing mMD8 (hereinafter referred to as an mMD8 virus) was prepared in accordance with a known protocol ["A Practical Guide for using the AdEasy System" (available on the internet at "coloncancer.org/adeasy.htm" coloncancer.org/adeasy/protocol2.htm)]. A control adenovirus solution (hereinafter referred to as a control virus) was prepared using pAdTrack-CMV instead of pAdTrack-CMV-mMD8.

(2) Construction of Adenovirus Vector for Expressing Human MD8 and Preparation of Adenovirus Solution PCR was performed by using pCEPdE2-MD8-FLAG prepared in Example 1(2) as a template, DNA consisting of the base sequence of SEQ ID NO: 23 as a 5' primer, DNA consisting of the base sequence of SEQ ID NO: 24 as a 3' primer, and DNA polymerase (Pyrobest DNA polymerase; Takara Shuzo). The PCR was carried out by performing a reaction at 95° C. for 2 minutes, repeating a cycle consisting of reactions at 98° C. for 20 seconds, at 55° C. for 30 seconds, and at 72° C. for 3 minutes 15 times, and performing a reaction at 72° C. for 7 minutes. The resulting DNA fragment of approximately 2.5 kbp was inserted at the EcoRV site of plasmid pZErO2.1 (Invitrogen) to construct pZErO-MD8-FLAG. The plasmid was digested with a restriction enzyme BglII, and then the resulting DNA fragment of approximately 2.5 kbp was inserted into and ligated with a pAdTrack-CMV vector (He T. C. et al., Proc. Natl. Acad. Sci. USA., 95, 2509-2514, 1998), which had been previously digested with a restriction enzyme BglII and dephosphorylated with alkaline phosphatase (BAPC75; Takara Shuzo). Among the clones, a clone in which the MD8-FLAG gene was located in the direction similar to the CMV promoter was selected to designated pAdTrack-CMV-MD8-FLAG. Hereinafter, an adenovirus solution having a high titer and expressing human MD8 (hereinafter referred to as an MD8 virus) was prepared in a manner similar to that in Example 4(1).

Example 5

Differentiation of 3T3-L1 to Adipocyte

A method for differentiation of a mouse 3T3-L1 cell (ATCC No.: CL-173) to an adipocyte was basically carried out in accordance with a known method (Ezaki et al., "IGAKU NO AYUMI (Journal of Clinical and Experimental Medicine", 503-506, 1998). The 3T3-L1 cell is a mouse-derived cultured cell strain which is widely used as a model cell of a white adipocyte.

The 3T3-L1 cells were plated on a 24-well collagen-coated plate (ASAHI TECHNO GLASS) to become 50000 cells per well. When the cells were confluent, the medium was changed to a Dulbecco's modified Eagle's medium (DMEM) supplemented with 0.5 mmol/L 3-isobutyl-1-methylxanthine, 0.25 µmol/L dexamethasone, and 10 µg/mL insulin and containing 10% fetal bovine serum to start the differentiation to adipocytes. After 2 days, the medium was changed to DMEM supplemented with only 1 µg/mL insulin and containing 10% fetal bovine serum, and then the medium change was repeated every three days to start an induction of differentiation.

Example 6

Infection of Adenovirus Vector (1) Preparation of Cells Infected with mMD8 Virus The mMD8 virus solution prepared in Example 4(1) was diluted with the medium to 100 µL ($2.2\times10^9$ viruses per well of a 24-well plate). The dilution was added to 3T3-L1 cells after 4 days from the induction of differentiation, without the cultured medium, to start infection. The plate was shaken every 20 minutes, and after shaking at 60 minutes, 400 µL of the medium was added and the culture was continued. A multiplicity of infection was calculated by visually observing fluorescence generated from green fluorescent protein (GFP) integrated into the prepared adenovirus by a fluorescent microscope, as a percentage of cells with fluorescence to all cells. To perform an experiment in glucose uptake shown in the following Examples, the 3T3-L1 cells cultured on the 24-well plate were divided into two groups, and infected with the mMD8 virus or control virus prepared in Example 4(1).

(2) Preparation of Cells Infected with MD8 Virus

The MD8 virus solution prepared in Example 4(2) was treated in a manner similar to that in Example 6(1), except for diluting the solution to $2.9\times10^9$ viruses per well of a 24-well plate, to prepare groups of 3T3-L1 cells infected with the MD8 virus or control virus prepared in Example 4(2).

Example 7

Measurement of Amount of Glucose Uptake into Adipocyte

The 3T3-L1 cells infected with adenovirus in Example 6 were cultured for 2 days, to progress infection and differentiation to adipocytes simultaneously. At the night after 7 days from the induction of differentiation, each well was washed twice with DMEM without serum, 500 µL of DMEM without serum was added to each well, and the plate was allowed to stand for a day. At the experimental day, each well was washed twice with a KRP buffer (136 mmol/L NaCl, 4.7 mmol/L KCl, 1.25 mmol/L $CaCl_2$, 1.25 mmol/L $MgSO_4$, and 5 mmol/L $Na_2HPO_4$), and the KRP buffer containing 1 µmol/L of insulin was added and incubated for 20 minutes. The similar procedure was performed except for using the KRP buffer without insulin, as a control.

To each well, 0.2 mmol/L 2-deoxyglucose (Wako Pure Chemical Industries) and 5.55 kBq 2-deoxy-D-(U-$^{14}$C) glucose (Amersham) was added and incubated for 10 minutes to chase glucose uptake. After washing three times with the ice-cold KRP buffer, cells were lysed with 150 µL of a 0.2% SDS solution and mixed well with aquasol-2 (Packard) to measure radioactivity incorporated into cells by a liquid scintillation counter (Packard).

The results when using the cells prepared in Example 6(1) are shown in FIG. 1. An amount of glucose uptake by an insulin stimulation was increased by approximately 3.4-fold in the adipocyte infected with the control virus, whereas the amount was increased by only approximately 2.4-fold in the adipocyte infected with the mMD8 virus. It is considered from the results that mMD8 inhibits glucose uptake. In this connection, the multiplicity of infection in this experiment was approximately 50%.

Figure 2:
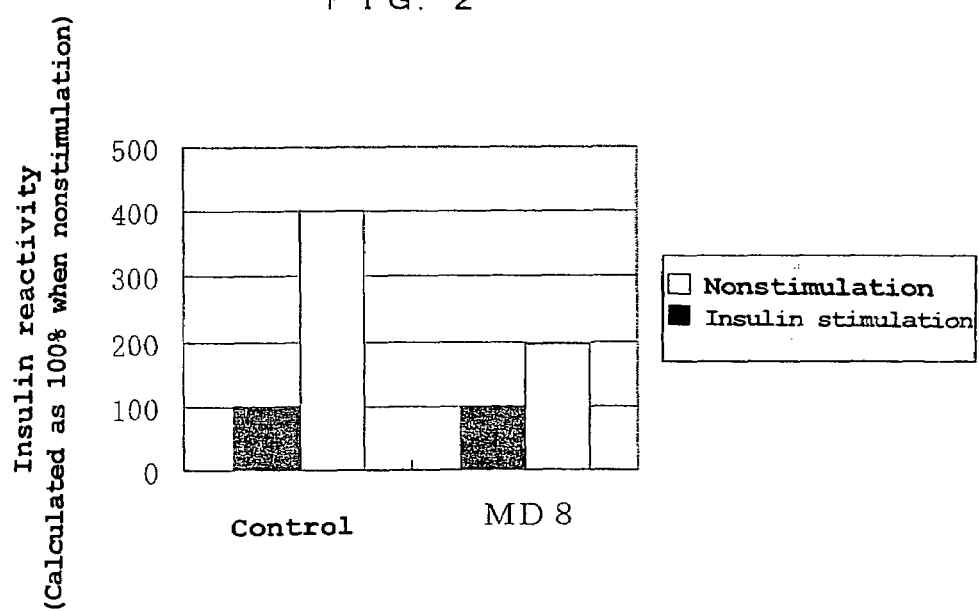
FIG. 2 is a graph showing amounts of glucose uptake by an insulin stimulation in differentiated adipocytes infected with the MD8 virus or control virus.

The results when using the cells prepared in Example 6(2) are shown in FIG. 2. An amount of glucose uptake by an insulin stimulation was increased by approximately 4.0-fold, in comparison to nonstimulation, in the adipocyte infected with the control virus, whereas the amount was increased by only approximately 2.0-fold, in comparison to nonstimulation, in the adipocyte infected with the MD8 virus. Similarly to mMD8, it is considered from the results that MD8 inhibits glucose uptake. In this connection, the multiplicity of infection in this experiment was approximately 70%.

Example 8

Confirmation of Activity of Digesting IGFBP by MD8S Protein (1) Preparation of Purified MD8S Enzyme Solution The expression plasmid pCEPdE2-MD8S-FLAG prepared in Example 1(3) was introduced into HEK293-EBNA cells (Invitrogen) with a transfection reagent (FuGENE™6 Transfection Reagent; Boeringer Mannheim) in accordance with a manual attached to the reagent. After 16 hours from the introduction of the expression plasmid, the medium was changed to a serum-free medium. The culture was continued for 2 days to collect the culture supernatant.

The MD8S protein from the culture supernatant was purified by affinity utilizing the FLAG tag added to the C-terminus. More particularly, the culture supernatant was applied to an M2-agarose (Sigma) column, the column was washed with 20 mmol/L tris-HCl(pH7.4)/150 mmol/L NaCl (hereinafter referred to as TBS), and elution and fractionation were performed with 100 µg/mL FLAG peptide (Sigma) in TBS to obtain an MD8S enzyme solution.

(2) Confirmation of Activity of Digesting IGFBP by MD8S Protein

The MD8S enzyme solution obtained in Example 8(1) was reacted with commercially available IGFBP-3 or IGFBP-5 (upstate biotechnology) in a 50 mmol/L tris-HCl (pH7.4) buffer containing 50 mmol/L NaCl, 2 mmol/L CaCl$_2$, 20 µg/mL bovine serum albumin (BSA), and 0.1% CHAPS at 37° C. overnight. In this connection, concentrations of the MD8S protein and IGFBP-3 (or IGFBP-5) in the reaction solution were 1.5 µg/mL and 10 µg/mL, respectively.

Using an aliquot of the reaction solution, sodium dodecyl sulfate polyacrylamide gel electrophoresis (SDS-PAGE) was carried out, and then a transfer to a PVDF membrane and blocking was carried out. IGFBP-3 was detected using an anti-IGFBP-3 polyclonal antibody (R&D System) as the first antibody and a peroxidase-labeled rabbit anti-goat IgG polyclonal antibody (ZYMED) as the second antibody. IGFBP-5 was detected using an anti-IGFBP-5 polyclonal antibody (upstate biotechnology) as the first antibody and a peroxidase-labeled goat anti-rabbit IgG polyclonal antibody (MBL) as the second antibody.

IGFBP-3 and IGFBP-5 were detected at approximately 45 kDa and 30 kDa, respectively. When the MD8S enzyme solution was added to each, a new band of 25 kDa was detected in the case of IGFBP-3, and new plural bands within the range of 12 to 25 kDa were detected in the case of IGFBP-5. It was found from the results that the MD8S protein exhibits an activity of digesting IGFBP-3 and IGFBP-5.

Example 9

Confirmation of Activity of Digesting Recombinant IGFBP-5 by MD8S (1) Preparation of Recombinant IGFBP-5 PCR was performed by using human placenta CDNA (Marathon-Ready™ cDNA; Clontech) as a template, oligo DNA consisting of the base sequence of SEQ ID NO: 25 (having the restriction enzyme XbaI recognition sequence added to the 5' terminus of the base sequence of the IGFBP-5 ORF of GenBank Accession No. M62782) and oligo DNA consisting of the base sequence of SEQ ID NO: 26 (having the restriction enzyme BamHI recognition sequence added to the 3' terminus of the base sequence of the IGFBP-5 ORF of GenBank Accession No. M62782) as primers, and LAtaqDNA polymerase (Takara Shuzo). The PCR was carried out by performing a reaction at 94° C. for 2 minutes, repeating a cycle consisting of reactions at 98° C. for 10 seconds, at 60° C. for 20 seconds, and at 72° C. for 1 minute 40 times, and performing a reaction at 72° C. for 7 minutes. The resulting DNA fragment of approximately 0.8 kbp was subcloned into plasmid PCRII (Invitrogen). The base sequence was analyzed using a DNA sequencer (ABI3700 DNA Sequencer; Applied Biosystems) by a dideoxy terminator method to designate plasmid pCRII-IGFBP5. The plasmid PCRII-IGFBP5 was digested with restriction enzymes XbaI and BamHI, and the resulting DNA fragment of approximately 0.8 kbp was inserted between the XbaI site and BamHI site of the plasmid pCEPdE2-FLAG to construct plasmid pCEPdE2-IGFBP5-FLAG to express a IGFBP-5-FLAG protein having the FLAG tag of SEQ ID NO: 12 added to the C-terminus of the full-length IGFBP-5 protein (272 amino acids: SWISS PROT Accession No. P24593).

The procedure described in Example 8(1) was repeated, except for using the plasmid pCEPdE2-IGFBP5-FLAG instead of the expression plasmid pCEPdE2-MD8S-FLAG, to prepare recombinant IGFBP-5.

(2) Confirmation of Activity of Digesting Recombinant IGFBP-5 by MD8S

The MD8S enzyme solution obtained in Example 8(1) was reacted with recombinant IGFBP-5 obtained in Example 9(1) in a 50 mmol/L tris-HCl (pH7.4) buffer containing 50 mmol/L NaCl, 2 mmol/L CaCl2, 20 µg/mL bovine serum albumin (BSA), and 0.1% CHAPS at 37° C. overnight. In this connection, concentrations of the MD8S protein and recombinant IGFBP-5 in the reaction solution were 1.5 µg/mL and 10 µg/mL, respectively.

Using an aliquot of the reaction solution, SDS-PAGE was carried out, and then a transfer to a PVDF membrane and blocking was carried out. Recombinant IGFBP-5 was detected by reacting a biotinylated M2 antibody (Sigma) as the first antibody, followed by a horseradish peroxidase-labeled streptavidin (Amersham) as the second antibody, and by using an ECL Western Blotting Detecting System (Amersham Pharmacia).

It was confirmed that recombinant IGFBP-5, which was detected in the control without the MD8S enzyme solution, was made to disappear by adding the MD8S enzyme solution. It was also confirmed from the result that the MD8S protein exhibits an activity of digesting IGFBP-5.

Example 10

Screening of MD8S Inhibitor

Substances inhibiting the activity of digesting IGFBP-5 by the MD8S protein can be screened by the reaction system utilizing western blotting performed in Example 9(2). In this Example, the procedure described in Example 9(2) was repeated, except that various compounds having a hydroxamic acid scaffold as a compound to be tested were added to the reaction system containing the MD8S enzyme solution and recombinant IGFBP-5, to measure an inhibitory intensity of the activity of digesting IGFBP-5.

To calculate the intensity of the inhibition activity ($IC_{50}$), the degree of the inhibition activity in each concentration of the compounds to be tested was examined by performing image processing of the image on the film obtained by western blotting, using a scanner (ES-2200; Epson).

The criterion for screening substances inhibiting the activity of digesting IGFBP-5 was 10 μmol/L or less in the intensity of the inhibition activity ($IC_{50}$). $N^{\alpha}$-[(3-carboxy-4-methylthio-2-propoxymethyl)butyryl]-N,O-dimethylthyrosineamide (WO93/09090; hereinafter referred to as compound A) was selected by this screening system. The intensity of the inhibition activity ($IC_{50}$) of the compound A was 3.3 μmol/L.

In this connection, the compound A can be synthesized by the method described in Example 5 of WO93/09090.

Figure 3:
FIG. 3 is a drawing showing the results of electrophoresis which shows that an activity of digesting recombinant IGFBP-3 and IGFBP-5 by the MD8S protein obtained in Example 10 was inhibited by the compound A.

As a sample of screening, the result when using the compound A as a compound to be tested is shown in FIG. 3.

In FIG. 3, lane 1 shows the result when incubating only recombinant IGFBP-5, and lane 2 shows the result when incubating recombinant IGFBP-5 and the MD8S enzyme solution. Lanes 3 to 7 show the results when incubating recombinant IGFBP-5 and the MD8S enzyme solution in the presence of the compound A. Concentrations of the compound A in lanes 3 to 7 are 10 μmol/L, 1 μmol/L, 100 nmol/L, 10 nmol/L, and 1 nmol/L, respectively. The arrow indicates the position of IGFBP-5.

Example 11

Cloning of Base Sequence of 5' Upstream of Human MD8 Gene ORF

PCR was performed by using human genome (Genomic DNA; Clontech) as a template, oligo DNAs consisting of the base sequence of SEQ ID NO: 21 or SEQ ID NO: 22 as primers, and DNA polymerase (Pyrobest DNA polymerase™; Takara Shuzo). The PCR was carried out by performing a reaction at 97° C. for 3 minutes, repeating a cycle consisting of reactions at 97° C. for 30 seconds, at 60° C. for 30 seconds, and at 72° C. for 2 minutes 40 times, and performing a reaction at 72° C. for 7 minutes. The resulting fragment of approximately 2 kbp consisting of the base sequence of SEQ ID NO: 20 was subcloned into a cloning vector (pCR4Blunt-TOPO;Invitrogen).

The resulting subclone was treated with BamHI and HindIII, and the obtained fragment consisting of the base sequence of the 34th to 2014th bases in the base sequence of SEQ ID NO: 20 was cloned into a vector for a luciferase assay system (PicaGene Vector 2 basic vector; Toyo Ink MFG) which had been previously treated with BglII and HindIII, to obtain pGV-B2-ADAM8pro2k.

Example 12

Analysis of DNA Sequence of Human MD8 Promoter Region

Figure 4:
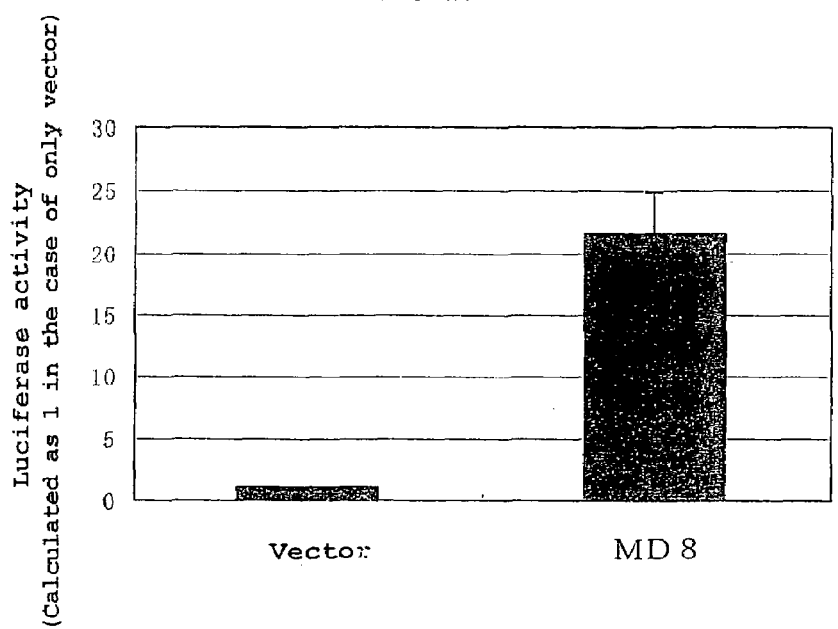
FIG. 4 is a graph showing the results of a luciferase assay using the MD8 promoter region.

The plasmid pGV-B2-ADAM8pro2k obtained in Example 11 was introduced into HEK293-EBNA cells (Invitrogen) cultured in a Dulbecco's modified Eagle's medium (DMEM) containing 10% fetal bovine serum, 100 μg/mL penicillin, 100 μg/mL streptomycin, and 250 μg/mL G418 (Nakarai Tesque) using a transfection reagent (FuGene-6; Nippon Roche). A luciferase activity after culturing for 36 or 48 hours under conventional culture conditions was measured with a commercially available measuring kit (PicaGene coloring kit; Toyo Ink MFG). In this connection, the measured values were compensated with the values of a β-gal activity expressed by a β-gal expression plasmid (pCH110; Amersham Pharmacia Biotech) which was co-introduced. The activity of β-gal was measured by a commercially available measuring kit (Galacto-Light Plus kit; Roche). As a result, an increased activity of luciferase, which was not detected in the original plasmid pGV-B2, was clearly observed (FIG. 4). This result shows that a promoter activity exists in the DNA fragment.

Referential Example 1

Measurement of Amount of MD8 Gene Expressed in Normal Mice and Diabetes Model Mice Genes of which increased amounts were expressed in diabetes model mice were examined in a preliminary experiment using a gene chip. As a result, it was found that the increased gene of GenBank Accession No. X13335 was expressed. The following experiment was performed to confirm whether or not an amount of expression was actually increased in the diabetes model mice.

In this Referential Example, an amount of mRNA expression of GenBank Accession No. X13335 in epididymal fat of two diabetes model mice KKAy/Ta (Iwatsuka et al., Endocrinol. Japon., 17, 23-35, 1970) and C57BL/KsJ-db/db (Kaku et al., Diabetologia, 32, 636-643, 1989) was measured by a real time PCR method using a sequence detector (ABI PRISM-7700 Sequence Detector; Applied Biosystems), and compared to those of normal mice C57BL/6J and C57BL/KsJ-+m/+m.

(1) Extirpation of Mouse Tissue

Male C57BL/6J, KKAy/Ta, C57BL/KsJ-+m/+m, and C57BL/KsJ-db/db mice (eight mice per each) were purchased from CLEA JAPAN.

C57BL/6J mice were bred collectively with normal diet until 12 weeks old. KKAy/Ta mice were bred separately with a high calorie diet (CMF; Oriental Yeast Co., Ltd.) until 12 weeks old. C57BL/KsJ-+m/+m mice and C57BL/KsJ-db/db mice were bred collectively with normal diet until 12 weeks old.

It was confirmed that KKAy/Ta mice and C57BL/KsJ-db/db mice exhibited hyperglycemia and a high weight in comparison with normal mice (KKAy/Ta mice: blood glucose level=447.1±4.2 mg/dL, weight=45.9±0.6 g; C57BL/KsJ-db/db mice: blood glucose level=423.7±14.1 mg/dL, weight=48.6±0.5 g). These four kinds of mice were anesthetized with diethyl ether to extirpate epididymal fat. Each epididymal fat was quickly frozen with liquid nitrogen and kept at −80° C.

(2) Extraction of Total RNA

Each tissue obtained in Reference Example 1(1) was cracked by a frozen cell crasher (CRYO-PRESS CP-100; MICROTEC NITION). An RNA extraction reagent (ISOGEN; Nippon Gene) was added and the mixture was homogenized by a homogenizer (ULTRA-TURRAX T-8; IKA LABORTECHNIK). RNA was extracted from each sample in accordance with a protocol of the RNA extraction reagent (ISOGEN). The extract was treated with DNase (Nippon Gene) to digest contaminated DNA. Phenol/chloroform treatment and ethanol precipitation were performed. An RNA concentration was determined by measuring absorbance at 260 nm and 280 nm with a spectrometer (U-2000; Hitachi). RNA was diluted with water to 10 ng/μL, and kept at −20° C.

(3) Preparation of Primers and TaqMan™ Probe

A TaqMan™ probe, a 5'-primer, and a 3'-primer used in a reverse transcriptase-polymerase chain reaction (RT-PCR) were designed by searching appropriate sites using an analysis software (Primer Express; Applied Biosystems) on the basis of the sequence of the gene registered as Accession No. X13335 in the GenBank database. More particularly, the DNA consisting of the base sequence of SEQ ID NO: 3 and the DNA consisting of the base sequence of SEQ ID NO: 4 were used as the 5'-primer and 3'-primer, respectively, and the DNA consisting of the base sequence of SEQ ID NO: 5 was used as the TaqMan™ probe.

The 5'-primer and 3'-primer were synthesized by GENSET. The TaqMan™ probe wherein the 5' terminus was labeled with a fluorescent dye FAM (6-carboxy-fluorescein) and the 3' terminus was labeled with a fluorescent dye TAMRA (6-carboxy-tetramethyl-rhodamine) was prepared by Applied Biosystems.

(4) Measurement of Amount of mRNA Expression

An expression level of mRNA contained in the total RNA derived from epididymal fat and amplified by the primers, that is, which was considered as X13335, was determined by a sequence detector (ABI PRISM™ 7700 Sequence Detector; Applied Biosystems). According to this detection system, the time course of amounts of DNA strands amplified in each step of RT-PCR can be monitored by detecting a fluorescent signal, and the amount of mRNA expression can be quantified on the basis of the cycle number of PCR over a certain fluorescent strength.

A RT-PCR solution was prepared using a commercially available kit (TaqMan EZ RT-PCR Core Reagents; Applied Biosystems) in accordance with a protocol thereof. The RT-PCR was carried out by performing an RT reaction consisting of reactions at 55° C. for 50 minutes, at 60° C. for 10 minutes, and at 95° C. for 2 minutes and then repeating a PCR reaction consisting of reactions at 95° C. for 15 seconds and at 58° C. for 1.5 minutes 40 times. Aliquots (4 ng, 20 ng, 100 ng, and 500 ng per tube) of the total RNA prepared from epididymal fat of the KKAy/Ta mouse were added to tubes, and then RT-PCR was carried out together with samples to determine a standard line. The amounts of gene expression were compensated with those of 18S rRNA contained in the samples.

As a result, with respect to the mRNA considered as X13335, the amount of expression in the diabetes model KKAy/Ta mice was increased by approximately 10-fold in comparison with that in the normal C57BL/6J mice, and the amount of expression in the diabetes model C57BL/KsJ-db/db mice was increased by approximately 110-fold in comparison with that in the normal C57BL/KsJ-m+/m+mice as a control.

From the results, it is considered that the expression of the X13335 gene is increased in diabetes models.

INDUSTRIAL APPLICABILITY

According to the screening tool or screening method of the present invention, a therapeutic agent for diabetes, particularly an agent for alleviating insulin resistance, can be screened.

The novel polypeptide of the present invention exhibits an activity of inhibiting glucose uptake into an adipocyte by an insulin stimulation, and thus can be used for the screening tool or screening method of the present invention.

The polynucleotide, vector, and transformant of the present invention are useful in manufacturing the polypeptide of the present invention.

The promoter of the present invention can also be used for the screening tool or screening method of the present invention. The transformant of the present invention comprising the polynucleotide or promoter of the present invention can be used for the screening tool or screening method of the present invention.

The probe of the present invention can be used for analyzing an amount of a polynucleotide encoding the polypeptide of the present invention. Diabetes can be diagnosed by an increase in the amount of the polynucleotide expressed as an indicator.

FREE TEXT IN SEQUENCE LISTING

Features of "Artificial Sequence" are described in the numeric identifier <223> in the Sequence Listing.

More particularly, each of the base sequences of SEQ ID NOS: 8, 9, 11, 18, 19, and 22-26 is an artificially synthesized primer sequence.

The amino acid sequence of SEQ ID NO: 12 is a FLAG tag amino acid sequence.

The symbol "Xaa" in the amino acid sequence of SEQ ID NO: 15 means an arbitrary amino acid.

The amino acid sequence of SEQ ID NO: 20 is a sequence containing a promoter sequence of human MD8 gene.

Although the present invention has been described with reference to specific embodiments, various changes and modifications obvious to those skilled in the art are possible without departing from the scope of the appended claims.

The invention claimed is:

1. An isolated polypeptide comprising the amino acid sequence of SEQ ID NO:2, wherein said polypeptide cleaves the insulin-like growth factor binding proteins 3 and 5.

2. An isolated polypeptide consisting of the amino acid sequence of SEQ ID NO: 2, wherein said polypeptide cleaves the insulin-like growth factor binding proteins 3 and 5.

* * * * *

SEQUENCE LISTING

<160> NUMBER OF SEQ ID NOS: 26

<210> SEQ ID NO 1
<211> LENGTH: 2475
<212> TYPE: DNA

```
<213> ORGANISM: Homo sapiens
<220> FEATURE:
<221> NAME/KEY: CDS
<222> LOCATION: (1)..(2475)
<223> OTHER INFORMATION:

<400> SEQUENCE: 1 atg cgc ggc ctc ggg ctc tgg ctg ctg ggc gcg atg atg ctg cct gcg     48
Met Arg Gly Leu Gly Leu Trp Leu Leu Gly Ala Met Met Leu Pro Ala
1               5                   10                  15 att gcc ccc agc cgg ccc tgg gcc ctc atg gag cag tat gag gtc gtg     96
Ile Ala Pro Ser Arg Pro Trp Ala Leu Met Glu Gln Tyr Glu Val Val
                20                  25                  30 ttg ccg cgg cgt ctg cca ggc ccc cga gtc cgc cga gct ctg ccc tcc    144
Leu Pro Arg Arg Leu Pro Gly Pro Arg Val Arg Arg Ala Leu Pro Ser
            35                  40                  45 cac ttg ggc ctg cac cca gag agg gtg agc tac gtc ctt ggg gcc aca    192
His Leu Gly Leu His Pro Glu Arg Val Ser Tyr Val Leu Gly Ala Thr
        50                  55                  60 ggg cac aac ttc acc ctc cac ctg cgg aag aac agg gac ctg ctg ggt    240
Gly His Asn Phe Thr Leu His Leu Arg Lys Asn Arg Asp Leu Leu Gly
65                  70                  75                  80 tcc ggc tac aca gag acc tat acg gct gcc aat ggc tcc gag gtg acg    288
Ser Gly Tyr Thr Glu Thr Tyr Thr Ala Ala Asn Gly Ser Glu Val Thr
                85                  90                  95 gag cag cct cgc ggg cag gac cac tgc ttc tac cag ggc cac gta gag    336
Glu Gln Pro Arg Gly Gln Asp His Cys Phe Tyr Gln Gly His Val Glu
                100                 105                 110 ggg tac ccg gac tca gcc gcc agc ctc agc acc tgt gcc ggc ctc agg    384
Gly Tyr Pro Asp Ser Ala Ala Ser Leu Ser Thr Cys Ala Gly Leu Arg
            115                 120                 125 ggt ttc ttc cag gtg ggg tca gac ctg cac ctg atc gag ccc ctg gat    432
Gly Phe Phe Gln Val Gly Ser Asp Leu His Leu Ile Glu Pro Leu Asp
        130                 135                 140 gaa ggt ggc gag ggc gga cgg cac gcc gtg tac cag gct gag cac ctg    480
Glu Gly Gly Glu Gly Gly Arg His Ala Val Tyr Gln Ala Glu His Leu
145                 150                 155                 160 ctg cag acg gcc ggg acc tgc ggg gtc agc gac gac agc ctg ggc agc    528
Leu Gln Thr Ala Gly Thr Cys Gly Val Ser Asp Asp Ser Leu Gly Ser
                165                 170                 175 ctc ctg gga ccc cgg acg gca gcc gtc ttc agg cct cgg ccc ggg gac    576
Leu Leu Gly Pro Arg Thr Ala Ala Val Phe Arg Pro Arg Pro Gly Asp
                180                 185                 190 tct ctg cca tcc cga gag acc cgc tac gtg gag ctg tat gtg gtc gtg    624
Ser Leu Pro Ser Arg Glu Thr Arg Tyr Val Glu Leu Tyr Val Val Val
            195                 200                 205 gac aat gca gag ttc cag atg ctg ggg agc gaa gca gcc gtg cgt cat    672
Asp Asn Ala Glu Phe Gln Met Leu Gly Ser Glu Ala Ala Val Arg His
        210                 215                 220 cgg gtg ctg gag gtg gtg aat cac gtg gac aag cta tat cag aaa ctc    720
Arg Val Leu Glu Val Val Asn His Val Asp Lys Leu Tyr Gln Lys Leu
225                 230                 235                 240 aac ttc cgt gtg gtc ctg gtg ggc ctg gag att tgg aat agt cag gac    768
Asn Phe Arg Val Val Leu Val Gly Leu Glu Ile Trp Asn Ser Gln Asp
                245                 250                 255 agg ttc cac gtc agc ccc gac ccc agt gtc aca ctg gag aac ctc ctg    816
Arg Phe His Val Ser Pro Asp Pro Ser Val Thr Leu Glu Asn Leu Leu
                260                 265                 270 acc tgg cag gca cgg caa cgg aca cgg cgg cac ctg cat gac aac gta    864
Thr Trp Gln Ala Arg Gln Arg Thr Arg Arg His Leu His Asp Asn Val
            275                 280                 285
```

|  |  |
|---|---:|
| cag ctc atc acg ggt gtc gac ttc acc ggg act act gtg ggg ttt gcc<br>Gln Leu Ile Thr Gly Val Asp Phe Thr Gly Thr Thr Val Gly Phe Ala<br>290                            295                         300 | 912 |
| agg gtg tcc gcc atg tgc tcc cac agc tca ggg gct gtg aac cag gac<br>Arg Val Ser Ala Met Cys Ser His Ser Ser Gly Ala Val Asn Gln Asp<br>305                            310                        315                 320 | 960 |
| cac agc aag aac ccc gtg ggc gtg gcc tgc acc atg gcc cat gag atg<br>His Ser Lys Asn Pro Val Gly Val Ala Cys Thr Met Ala His Glu Met<br>                      325                        330                       335 | 1008 |
| ggc cac aac ctg ggc atg gac cat gat gag aac gtc cag ggc tgc cgc<br>Gly His Asn Leu Gly Met Asp His Asp Glu Asn Val Gln Gly Cys Arg<br>              340                        345                        350 | 1056 |
| tgc cag gaa cgc ttc gag gcc ggc cgc tgc atc atg gca ggc agc att<br>Cys Gln Glu Arg Phe Glu Ala Gly Arg Cys Ile Met Ala Gly Ser Ile<br>                      355                        360                       365 | 1104 |
| ggc tcc agt ttc ccc agg atg ttc agt gac tgc agc cag gcc tac ctg<br>Gly Ser Ser Phe Pro Arg Met Phe Ser Asp Cys Ser Gln Ala Tyr Leu<br>370                            375                        380 | 1152 |
| gag agc ttt ttg gag cgg ccg cag tcg gtg tgc ctc gcc aac gcc cct<br>Glu Ser Phe Leu Glu Arg Pro Gln Ser Val Cys Leu Ala Asn Ala Pro<br>385                            390                        395                 400 | 1200 |
| gac ctc agc cac ctg gtg ggc ggc ccc gtg tgt ggg aac ctg ttt gtg<br>Asp Leu Ser His Leu Val Gly Gly Pro Val Cys Gly Asn Leu Phe Val<br>                         405                        410                       415 | 1248 |
| gag cgt ggg gag cag tgc gac tgc ggc ccc ccc gag gac tgc cgg aac<br>Glu Arg Gly Glu Gln Cys Asp Cys Gly Pro Pro Glu Asp Cys Arg Asn<br>                      420                        425                       430 | 1296 |
| cgc tgc tgc aac tct acc acc tgc cag ctg gct gag ggg gcc cag tgt<br>Arg Cys Cys Asn Ser Thr Thr Cys Gln Leu Ala Glu Gly Ala Gln Cys<br>              435                        440                        445 | 1344 |
| gcg cac ggt acc tgc tgc cag gag tgc aag gtg aag ccg gct ggt gag<br>Ala His Gly Thr Cys Cys Gln Glu Cys Lys Val Lys Pro Ala Gly Glu<br>450                            455                        460 | 1392 |
| ctg tgc cgt ccc aag aag gac atg tgt gac ctc gag gag ttc tgt gac<br>Leu Cys Arg Pro Lys Lys Asp Met Cys Asp Leu Glu Glu Phe Cys Asp<br>465                            470                        475                 480 | 1440 |
| ggc cgg cac cct gag tgc ccg gaa gac gcc ttc cag gag aac ggc acg<br>Gly Arg His Pro Glu Cys Pro Glu Asp Ala Phe Gln Glu Asn Gly Thr<br>                      485                        490                       495 | 1488 |
| ccc tgc tcc ggg ggc tac tgc tac aac ggg gcc tgt ccc aca ctg gcc<br>Pro Cys Ser Gly Gly Tyr Cys Tyr Asn Gly Ala Cys Pro Thr Leu Ala<br>                  500                        505                       510 | 1536 |
| cag cag tgc cag gcc ttc tgg ggg cca ggt ggg cag gct gcc gag gag<br>Gln Gln Cys Gln Ala Phe Trp Gly Pro Gly Gly Gln Ala Ala Glu Glu<br>              515                        520                        525 | 1584 |
| tcc tgc ttc tcc tat gac atc cta cca ggc tgc aag gcc agc cgg tac<br>Ser Cys Phe Ser Tyr Asp Ile Leu Pro Gly Cys Lys Ala Ser Arg Tyr<br>530                            535                        540 | 1632 |
| agg gct gac atg tgt ggc gtt ctg cag tgc aag ggt ggg cag cag ccc<br>Arg Ala Asp Met Cys Gly Val Leu Gln Cys Lys Gly Gly Gln Gln Pro<br>545                            550                        555                 560 | 1680 |
| ctg ggg cgt gcc atc tgc atc gtg gat gtg tgc cac gcg ctc acc aca<br>Leu Gly Arg Ala Ile Cys Ile Val Asp Val Cys His Ala Leu Thr Thr<br>                        565                        570                       575 | 1728 |
| gag gat ggc act gcg tat gaa cca gtg ccc gag ggc acc cgg tgt gga<br>Glu Asp Gly Thr Ala Tyr Glu Pro Val Pro Glu Gly Thr Arg Cys Gly<br>                      580                        585                       590 | 1776 |
| cca gag aag gtt tgc tgg aaa gga cgt tgc cag gac tta cac gtt tac<br>Pro Glu Lys Val Cys Trp Lys Gly Arg Cys Gln Asp Leu His Val Tyr | 1824 |

```
                595                 600                 605
aga tcc agc aac tgc tct gcc cag tgc cac aac cat ggg gtg tgc aac      1872
Arg Ser Ser Asn Cys Ser Ala Gln Cys His Asn His Gly Val Cys Asn
        610                 615                 620 cac aag cag gag tgc cac tgc cac gcg ggc tgg gcc ccg ccc cac tgc      1920
His Lys Gln Glu Cys His Cys His Ala Gly Trp Ala Pro Pro His Cys
625                 630                 635                 640 gcg aag ctg ctg act gag gtg cac gca gcg tcc ggg agc ctc ccc gtc      1968
Ala Lys Leu Leu Thr Glu Val His Ala Ala Ser Gly Ser Leu Pro Val
                645                 650                 655 ctc gtg gtg gtg gtt ctg gtg ctc ctg gca gtt gtg ctg gtc acc ctg      2016
Leu Val Val Val Val Leu Val Leu Leu Ala Val Val Leu Val Thr Leu
            660                 665                 670 gca ggc atc atc gtc tac cgc aaa gcc cgg agc cgc atc ctg agc agg      2064
Ala Gly Ile Ile Val Tyr Arg Lys Ala Arg Ser Arg Ile Leu Ser Arg
        675                 680                 685 aac gtg gct ccc aag acc aca atg ggg cgc tcc aac ccc ctg ttc cac      2112
Asn Val Ala Pro Lys Thr Thr Met Gly Arg Ser Asn Pro Leu Phe His
    690                 695                 700 cag gct gcc agc cgc gtg ccg gcc aag ggc ggg gct cca gcc cca tcc      2160
Gln Ala Ala Ser Arg Val Pro Ala Lys Gly Gly Ala Pro Ala Pro Ser
705                 710                 715                 720 agg ggc ccc caa gag ctg gtc ccc acc acc cac ccg ggc cag ccc gcc      2208
Arg Gly Pro Gln Glu Leu Val Pro Thr Thr His Pro Gly Gln Pro Ala
                725                 730                 735 cga cac ccg gcc tcc tcg gtg gct ctg aag agg ccg ccc cct gct cct      2256
Arg His Pro Ala Ser Ser Val Ala Leu Lys Arg Pro Pro Pro Ala Pro
            740                 745                 750 ccg gtc act gtg tcc agc cca ccc ttc cca gtt cct gtc tac acc cgg      2304
Pro Val Thr Val Ser Ser Pro Pro Phe Pro Val Pro Val Tyr Thr Arg
        755                 760                 765 cag gca cca aag cag gtc atc aag cca acg ttc gca ccc cca gtg ccc      2352
Gln Ala Pro Lys Gln Val Ile Lys Pro Thr Phe Ala Pro Pro Val Pro
    770                 775                 780 cca gtc aaa ccc ggg gct ggt gcg gcc aac cct ggt cca gct gag ggt      2400
Pro Val Lys Pro Gly Ala Gly Ala Ala Asn Pro Gly Pro Ala Glu Gly
785                 790                 795                 800 gct gtt ggc cca aag gtt gcc ctg aag ccc ccc atc cag agg aag caa      2448
Ala Val Gly Pro Lys Val Ala Leu Lys Pro Pro Ile Gln Arg Lys Gln
                805                 810                 815 gga gcc gga gct ccc aca gca ccc tag                                  2475
Gly Ala Gly Ala Pro Thr Ala Pro
            820

<210> SEQ ID NO 2
<211> LENGTH: 824
<212> TYPE: PRT
<213> ORGANISM: Homo sapiens

<400> SEQUENCE: 2

Met Arg Gly Leu Gly Leu Trp Leu Leu Gly Ala Met Met Leu Pro Ala
1               5                   10                  15

Ile Ala Pro Ser Arg Pro Trp Ala Leu Met Glu Gln Tyr Glu Val Val
                20                  25                  30

Leu Pro Arg Arg Leu Pro Gly Pro Arg Val Arg Arg Ala Leu Pro Ser
            35                  40                  45

His Leu Gly Leu His Pro Glu Arg Val Ser Tyr Val Leu Gly Ala Thr
        50                  55                  60

Gly His Asn Phe Thr Leu His Leu Arg Lys Asn Arg Asp Leu Leu Gly
```

```
                65                  70                  75                  80
        Ser Gly Tyr Thr Glu Thr Tyr Thr Ala Ala Asn Gly Ser Glu Val Thr
                            85                  90                  95
        Glu Gln Pro Arg Gly Gln Asp His Cys Phe Tyr Gln Gly His Val Glu
                        100                 105                 110
        Gly Tyr Pro Asp Ser Ala Ala Ser Leu Ser Thr Cys Ala Gly Leu Arg
                        115                 120                 125
        Gly Phe Phe Gln Val Gly Ser Asp Leu His Leu Ile Glu Pro Leu Asp
                    130                 135                 140
        Glu Gly Glu Gly Gly Arg His Ala Val Tyr Gln Ala Glu His Leu
        145                 150                 155                 160
        Leu Gln Thr Ala Gly Thr Cys Gly Val Ser Asp Asp Ser Leu Gly Ser
                            165                 170                 175
        Leu Leu Gly Pro Arg Thr Ala Ala Val Phe Arg Pro Arg Pro Gly Asp
                        180                 185                 190
        Ser Leu Pro Ser Arg Glu Thr Arg Tyr Val Glu Leu Tyr Val Val Val
                        195                 200                 205
        Asp Asn Ala Glu Phe Gln Met Leu Gly Ser Glu Ala Ala Val Arg His
                    210                 215                 220
        Arg Val Leu Glu Val Val Asn His Val Asp Lys Leu Tyr Gln Lys Leu
        225                 230                 235                 240
        Asn Phe Arg Val Val Leu Val Gly Leu Glu Ile Trp Asn Ser Gln Asp
                            245                 250                 255
        Arg Phe His Val Ser Pro Asp Pro Ser Val Thr Leu Glu Asn Leu Leu
                        260                 265                 270
        Thr Trp Gln Ala Arg Gln Arg Thr Arg Arg His Leu His Asp Asn Val
                        275                 280                 285
        Gln Leu Ile Thr Gly Val Asp Phe Thr Gly Thr Thr Val Gly Phe Ala
                    290                 295                 300
        Arg Val Ser Ala Met Cys Ser His Ser Ser Gly Ala Val Asn Gln Asp
        305                 310                 315                 320
        His Ser Lys Asn Pro Val Gly Val Ala Cys Thr Met Ala His Glu Met
                            325                 330                 335
        Gly His Asn Leu Gly Met Asp His Asp Glu Asn Val Gln Gly Cys Arg
                        340                 345                 350
        Cys Gln Glu Arg Phe Glu Ala Gly Arg Cys Ile Met Ala Gly Ser Ile
                        355                 360                 365
        Gly Ser Ser Phe Pro Arg Met Phe Ser Asp Cys Ser Gln Ala Tyr Leu
                    370                 375                 380
        Glu Ser Phe Leu Glu Arg Pro Gln Ser Val Cys Leu Ala Asn Ala Pro
        385                 390                 395                 400
        Asp Leu Ser His Leu Val Gly Pro Val Cys Gly Asn Leu Phe Val
                            405                 410                 415
        Glu Arg Gly Glu Gln Cys Asp Cys Gly Pro Pro Glu Asp Cys Arg Asn
                        420                 425                 430
        Arg Cys Cys Asn Ser Thr Thr Cys Gln Leu Ala Glu Gly Ala Gln Cys
                        435                 440                 445
        Ala His Gly Thr Cys Cys Gln Glu Cys Lys Val Lys Pro Ala Gly Glu
                    450                 455                 460
        Leu Cys Arg Pro Lys Lys Asp Met Cys Asp Leu Glu Glu Phe Cys Asp
        465                 470                 475                 480
        Gly Arg His Pro Glu Cys Pro Glu Asp Ala Phe Gln Glu Asn Gly Thr
                            485                 490                 495
```

```
Pro Cys Ser Gly Gly Tyr Cys Tyr Asn Gly Ala Cys Pro Thr Leu Ala
            500                 505                 510

Gln Gln Cys Gln Ala Phe Trp Gly Pro Gly Gln Ala Ala Glu Glu
        515                 520                 525

Ser Cys Phe Ser Tyr Asp Ile Leu Pro Gly Cys Lys Ala Ser Arg Tyr
530                 535                 540

Arg Ala Asp Met Cys Gly Val Leu Gln Cys Lys Gly Gln Gln Pro
545                 550                 555                 560

Leu Gly Arg Ala Ile Cys Ile Val Asp Val Cys His Ala Leu Thr Thr
                565                 570                 575

Glu Asp Gly Thr Ala Tyr Glu Pro Val Pro Glu Gly Thr Arg Cys Gly
            580                 585                 590

Pro Glu Lys Val Cys Trp Lys Gly Arg Cys Gln Asp Leu His Val Tyr
            595                 600                 605

Arg Ser Ser Asn Cys Ser Ala Gln Cys His Asn His Gly Val Cys Asn
        610                 615                 620

His Lys Gln Glu Cys His Cys His Ala Gly Trp Ala Pro Pro His Cys
625                 630                 635                 640

Ala Lys Leu Leu Thr Glu Val His Ala Ala Ser Gly Ser Leu Pro Val
                645                 650                 655

Leu Val Val Val Val Leu Val Leu Leu Ala Val Val Leu Val Thr Leu
            660                 665                 670

Ala Gly Ile Ile Val Tyr Arg Lys Ala Arg Ser Arg Ile Leu Ser Arg
            675                 680                 685

Asn Val Ala Pro Lys Thr Thr Met Gly Arg Ser Asn Pro Leu Phe His
        690                 695                 700

Gln Ala Ala Ser Arg Val Pro Ala Lys Gly Gly Ala Pro Ala Pro Ser
705                 710                 715                 720

Arg Gly Pro Gln Glu Leu Val Pro Thr Thr His Pro Gly Gln Pro Ala
                725                 730                 735

Arg His Pro Ala Ser Ser Val Ala Leu Lys Arg Pro Pro Pro Ala Pro
            740                 745                 750

Pro Val Thr Val Ser Ser Pro Pro Phe Pro Val Pro Val Tyr Thr Arg
            755                 760                 765

Gln Ala Pro Lys Gln Val Ile Lys Pro Thr Phe Ala Pro Pro Val Pro
        770                 775                 780

Pro Val Lys Pro Gly Ala Gly Ala Ala Asn Pro Gly Pro Ala Glu Gly
785                 790                 795                 800

Ala Val Gly Pro Lys Val Ala Leu Lys Pro Pro Ile Gln Arg Lys Gln
                805                 810                 815

Gly Ala Gly Ala Pro Thr Ala Pro
            820

<210> SEQ ID NO 3
<211> LENGTH: 23
<212> TYPE: DNA
<213> ORGANISM: Mus sp.

<400> SEQUENCE: 3
tgaggacatt ccaggatgct act                                         23

<210> SEQ ID NO 4
<211> LENGTH: 24
<212> TYPE: DNA
<213> ORGANISM: Mus sp.
```

```
<400> SEQUENCE: 4
gtcaatcttg ctacacctgc tgaa                                           24

<210> SEQ ID NO 5
<211> LENGTH: 26
<212> TYPE: DNA
<213> ORGANISM: Mus sp.

<400> SEQUENCE: 5
tgaccgaaag catcggctcc aagttc                                         26

<210> SEQ ID NO 6
<211> LENGTH: 27
<212> TYPE: DNA
<213> ORGANISM: Homo sapiens

<400> SEQUENCE: 6
gacccggcca tgcgcggcct cgggctc                                        27

<210> SEQ ID NO 7
<211> LENGTH: 28
<212> TYPE: DNA
<213> ORGANISM: Homo sapiens

<400> SEQUENCE: 7
attttccaca caggcgcagg tgcccccc                                       28

<210> SEQ ID NO 8
<211> LENGTH: 29
<212> TYPE: DNA
<213> ORGANISM: artificial sequence
<220> FEATURE:
<223> OTHER INFORMATION: Description of Artificial Sequence: an
      artificially synthesized primer sequence

<400> SEQUENCE: 8
gctctagagc catgcgcggc ctcgggctc                                      29

<210> SEQ ID NO 9
<211> LENGTH: 29
<212> TYPE: DNA
<213> ORGANISM: artificial sequence
<220> FEATURE:
<223> OTHER INFORMATION: Description of Artificial Sequence: an
      artificially synthesized primer sequence

<400> SEQUENCE: 9
cgggatccct cagtcagcag cttcgcgca                                      29

<210> SEQ ID NO 10
<211> LENGTH: 30
<212> TYPE: DNA
<213> ORGANISM: Homo sapiens

<400> SEQUENCE: 10
aaaggacgtt gccaggactt acacgtttac                                     30

<210> SEQ ID NO 11
<211> LENGTH: 38
<212> TYPE: DNA
<213> ORGANISM: artificial sequence
<220> FEATURE:
<223> OTHER INFORMATION: Description of Artificial Sequence: an
      artificially synthesized primer sequence
```

-continued

<400> SEQUENCE: 11
cgggatccgg gtgctgtggg agctccggct ccttgctt                    38

<210> SEQ ID NO 12
<211> LENGTH: 8
<212> TYPE: PRT
<213> ORGANISM: artificial sequence
<220> FEATURE:
<223> OTHER INFORMATION: Description of Artificial Sequence: a FLAG tag
      amino acid sequence

<400> SEQUENCE: 12

Asp Tyr Lys Asp Asp Asp Asp Lys
1               5

<210> SEQ ID NO 13
<211> LENGTH: 2587
<212> TYPE: DNA
<213> ORGANISM: Mus sp.
<220> FEATURE:
<221> NAME/KEY: CDS
<222> LOCATION: (17)..(2494)
<223> OTHER INFORMATION:

<400> SEQUENCE: 13

```
tgctccagat cccatc atg ctt ggc ctc tgg ctg ctc agc gtc tta tgg aca      52
                Met Leu Gly Leu Trp Leu Leu Ser Val Leu Trp Thr
                1               5                   10 cca gta gcc cct gga cct cct ttg ccc cat gtg aaa cag tat gaa gtg       100
Pro Val Ala Pro Gly Pro Pro Leu Pro His Val Lys Gln Tyr Glu Val
        15                  20                  25 gtt tgg cct cgg cgc cta gct gca tcc cgc tcc cgc aga gcc ctg ccc       148
Val Trp Pro Arg Arg Leu Ala Ala Ser Arg Ser Arg Arg Ala Leu Pro
    30                  35                  40 tcc cac tgg ggc cag tac cca gag agt ctg agc tat gct ctt ggg acc       196
Ser His Trp Gly Gln Tyr Pro Glu Ser Leu Ser Tyr Ala Leu Gly Thr
45                  50                  55                  60 agc ggg cac gtt ttc acc ctg cac ctt cga aag aac agg gac ctg ctg       244
Ser Gly His Val Phe Thr Leu His Leu Arg Lys Asn Arg Asp Leu Leu
                65                  70                  75 ggc tca agc tac aca gag acc tac tca gct gcc aat ggc tct gag gtg       292
Gly Ser Ser Tyr Thr Glu Thr Tyr Ser Ala Ala Asn Gly Ser Glu Val
            80                  85                  90 aca gag caa ctg cag gag cag gac cat tgc ctc tac caa ggc cat gtg       340
Thr Glu Gln Leu Gln Glu Gln Asp His Cys Leu Tyr Gln Gly His Val
        95                  100                 105 gaa ggg tac gag ggc tca gct gcc agt att agc acc tgt gct ggc ctc       388
Glu Gly Tyr Glu Gly Ser Ala Ala Ser Ile Ser Thr Cys Ala Gly Leu
    110                 115                 120 agg ggc ttt ttc cga gtt ggg tcc act gtc cac ttg att gag cct ctg       436
Arg Gly Phe Phe Arg Val Gly Ser Thr Val His Leu Ile Glu Pro Leu
125                 130                 135                 140 gat gct gat gaa gag ggg caa cat gcg atg tat cag gca aag cat ctg       484
Asp Ala Asp Glu Glu Gly Gln His Ala Met Tyr Gln Ala Lys His Leu
                145                 150                 155 caa cag aag gct ggg acc tgt ggg gtc aaa gat acc aac ctg aat gac       532
Gln Gln Lys Ala Gly Thr Cys Gly Val Lys Asp Thr Asn Leu Asn Asp
            160                 165                 170 cta ggg cct cgg gca tta gaa ata tac agg gct cag cca cgg aac tgg       580
Leu Gly Pro Arg Ala Leu Glu Ile Tyr Arg Ala Gln Pro Arg Asn Trp
        175                 180                 185
```

```
ctg ata ccc aga gaa acc cgc tat gtg gag ttg tat gtg gtt gca gac      628
Leu Ile Pro Arg Glu Thr Arg Tyr Val Glu Leu Tyr Val Val Ala Asp
    190             195             200 agc caa gag ttc cag aag ttg ggg agc aga gag gcc gtg cgc cag cga      676
Ser Gln Glu Phe Gln Lys Leu Gly Ser Arg Glu Ala Val Arg Gln Arg
205             210             215                 220 gtg ctg gag gtt gta aac cac gtg gac aag ctt tat cag gaa ctc agt      724
Val Leu Glu Val Val Asn His Val Asp Lys Leu Tyr Gln Glu Leu Ser
                    225             230             235 ttc cga gtt gtc ctg gtg ggc ctg gag atc tgg aac aag gac aaa ttc      772
Phe Arg Val Val Leu Val Gly Leu Glu Ile Trp Asn Lys Asp Lys Phe
            240             245             250 tac atc agc cgc tat gcc aac gtg aca ctg gag aac ttc ttg tcc tgg      820
Tyr Ile Ser Arg Tyr Ala Asn Val Thr Leu Glu Asn Phe Leu Ser Trp
        255             260             265 agg gaa cag aac ttg caa ggg cag cac cca cat gac aac gtg caa ctt      868
Arg Glu Gln Asn Leu Gln Gly Gln His Pro His Asp Asn Val Gln Leu
    270             275             280 atc acg ggg gtt gat ttc att ggg agc act gtt gga ctg gct aag gtg      916
Ile Thr Gly Val Asp Phe Ile Gly Ser Thr Val Gly Leu Ala Lys Val
285             290             295             300 tct gcc ctg tgt tcc cgt cac tcc gga gct gtg aat cag gac cac tcc      964
Ser Ala Leu Cys Ser Arg His Ser Gly Ala Val Asn Gln Asp His Ser
                305             310             315 aag aac tcc att ggt gta gcc tcc acc atg gcc cat gag ctg ggc cac     1012
Lys Asn Ser Ile Gly Val Ala Ser Thr Met Ala His Glu Leu Gly His
            320             325             330 aac ctg ggc atg agc cat gat gag gac att cca gga tgc tac tgt cct     1060
Asn Leu Gly Met Ser His Asp Glu Asp Ile Pro Gly Cys Tyr Cys Pro
        335             340             345 gaa cca cgg gag ggt ggt ggc tgc atc atg acc gaa agc atc ggc tcc     1108
Glu Pro Arg Glu Gly Gly Gly Cys Ile Met Thr Glu Ser Ile Gly Ser
    350             355             360 aag ttc ccc agg ata ttc agc agg tgt agc aag att gac cta gag tca     1156
Lys Phe Pro Arg Ile Phe Ser Arg Cys Ser Lys Ile Asp Leu Glu Ser
365             370             375             380 ttc gtg aca aaa ccc cag aca ggc tgc ctg acc aat gtt cca gat gtc     1204
Phe Val Thr Lys Pro Gln Thr Gly Cys Leu Thr Asn Val Pro Asp Val
                385             390             395 aac cgg ttc gtg ggt ggc cct gtg tgt gga aac ctg ttt gtg gag cat     1252
Asn Arg Phe Val Gly Gly Pro Val Cys Gly Asn Leu Phe Val Glu His
            400             405             410 gga gag cag tgt gac tgt ggc aca cct cag gac tgt caa aac ccc tgc     1300
Gly Glu Gln Cys Asp Cys Gly Thr Pro Gln Asp Cys Gln Asn Pro Cys
        415             420             425 tgc aat gcc acc act tgc cag ctg gtc aag ggg gca gag tgt gcc agt     1348
Cys Asn Ala Thr Thr Cys Gln Leu Val Lys Gly Ala Glu Cys Ala Ser
    430             435             440 ggt acc tgt tgt cat gaa tgc aag gtg aag cca gct gga gag gtg tgt     1396
Gly Thr Cys Cys His Glu Cys Lys Val Lys Pro Ala Gly Glu Val Cys
445             450             455             460 cgt ctc agt aag gac aaa tgt gac ctg gag gag ttc tgt gat ggc cgg     1444
Arg Leu Ser Lys Asp Lys Cys Asp Leu Glu Glu Phe Cys Asp Gly Arg
                465             470             475 aag cca aca tgt ccc gaa gat gcc ttc caa cag aat ggc act ccc tgc     1492
Lys Pro Thr Cys Pro Glu Asp Ala Phe Gln Gln Asn Gly Thr Pro Cys
            480             485             490 cca ggg ggc tac tgc ttt gat ggg agc tgt ccc acc ctg gca cag cag     1540
Pro Gly Gly Tyr Cys Phe Asp Gly Ser Cys Pro Thr Leu Ala Gln Gln
        495             500             505
```

-continued

| | |
|---|---|
| tgc cgg gat ctg tgg ggg cca ggt gct cgg gta gca gcc gac tcc tgc<br>Cys Arg Asp Leu Trp Gly Pro Gly Ala Arg Val Ala Ala Asp Ser Cys<br>510                          515                    520 | 1588 |
| tat acc ttt agc atc cct ccg ggc tgc aat ggg agg atg tac tct ggc<br>Tyr Thr Phe Ser Ile Pro Pro Gly Cys Asn Gly Arg Met Tyr Ser Gly<br>525                          530                    535                    540 | 1636 |
| agg atc aac cgg tgt gga gcg ctg tac tgt gag gga ggc cag aag ccc<br>Arg Ile Asn Arg Cys Gly Ala Leu Tyr Cys Glu Gly Gly Gln Lys Pro<br>                    545                    550                    555 | 1684 |
| ctt gaa cgc tcc ttc tgc act ttc tcc tcc aac cat gga gtc tgc cat<br>Leu Glu Arg Ser Phe Cys Thr Phe Ser Ser Asn His Gly Val Cys His<br>          560                    565                    570 | 1732 |
| gct ctt ggc aca ggc agc aac att gac acc ttt gag ctg gta ttg cag<br>Ala Leu Gly Thr Gly Ser Asn Ile Asp Thr Phe Glu Leu Val Leu Gln<br>                    575                    580                    585 | 1780 |
| ggc acc aag tgc gag gag gga aag gtt tgc atg gat gga agc tgc cag<br>Gly Thr Lys Cys Glu Glu Gly Lys Val Cys Met Asp Gly Ser Cys Gln<br>590                          595                    600 | 1828 |
| gac ctc cgt gta tac aga tct gaa aac tgc tct gct aaa tgc aac aac<br>Asp Leu Arg Val Tyr Arg Ser Glu Asn Cys Ser Ala Lys Cys Asn Asn<br>605                          610                    615                    620 | 1876 |
| cat ggg gta tgc aac cac aag agg gag tgc cac tgt cac aag ggc tgg<br>His Gly Val Cys Asn His Lys Arg Glu Cys His Cys His Lys Gly Trp<br>                        625                    630                    635 | 1924 |
| gca cca ccc aac tgt gta cag cgg ctg gca gat gta tca gat gaa caa<br>Ala Pro Pro Asn Cys Val Gln Arg Leu Ala Asp Val Ser Asp Glu Gln<br>                    640                    645                    650 | 1972 |
| gca gcg tct acg agc ctc cca gtc agt gtg gtt gtg gtc ttg gtg atc<br>Ala Ala Ser Thr Ser Leu Pro Val Ser Val Val Val Val Leu Val Ile<br>          655                    660                    665 | 2020 |
| ctg gtg gct gcg atg gtc atc gtg gca ggc atc gtc atc tac cga aag<br>Leu Val Ala Ala Met Val Ile Val Ala Gly Ile Val Ile Tyr Arg Lys<br>670                          675                    680 | 2068 |
| gct ccg aga caa atc cag agg agg agt gtg gca ccc aag cct atc tcg<br>Ala Pro Arg Gln Ile Gln Arg Arg Ser Val Ala Pro Lys Pro Ile Ser<br>685                          690                    695                    700 | 2116 |
| ggg ctc tcc aac ccc cta ttc tac aca agg gac agc agc ctg cca gct<br>Gly Leu Ser Asn Pro Leu Phe Tyr Thr Arg Asp Ser Ser Leu Pro Ala<br>                    705                    710                    715 | 2164 |
| aag aac agg cct cca gac cct tct gag aca gtt tct acc aac cag ccc<br>Lys Asn Arg Pro Pro Asp Pro Ser Glu Thr Val Ser Thr Asn Gln Pro<br>                    720                    725                    730 | 2212 |
| cca aga ccc ata gtg aaa cca aag agg cct ccc cct gca cct cca ggt<br>Pro Arg Pro Ile Val Lys Pro Lys Arg Pro Pro Pro Ala Pro Pro Gly<br>          735                    740                    745 | 2260 |
| gct gtg tcc agt tca cca ctc cca gtt cct gtt tat gcc cca aag ata<br>Ala Val Ser Ser Ser Pro Leu Pro Val Pro Val Tyr Ala Pro Lys Ile<br>750                          755                    760 | 2308 |
| cca aat cag ttt aga cct gat cct ccc acc aag ccc ctc cca gag ctg<br>Pro Asn Gln Phe Arg Pro Asp Pro Pro Thr Lys Pro Leu Pro Glu Leu<br>765                          770                    775                    780 | 2356 |
| aaa ccc aag cag gtc aag cca acc ttt gca ccc cg aca cca cca gtc<br>Lys Pro Lys Gln Val Lys Pro Thr Phe Ala Pro Pro Thr Pro Pro Val<br>                    785                    790                    795 | 2404 |
| aag ccc ggg act gga ggg acg gtg cct gga gca act cag gga gct ggt<br>Lys Pro Gly Thr Gly Gly Thr Val Pro Gly Ala Thr Gln Gly Ala Gly<br>                    800                    805                    810 | 2452 |
| ggg cca aag gtt gct ctg aag gtc ccc atc cag aag agg tga<br>Gly Pro Lys Val Ala Leu Lys Val Pro Ile Gln Lys Arg | 2494 |

```
                    815                 820                 825 ccagctaggg caccccaggg ccatcgtttg tggacgtttg gagataccac tgctcctata      2554
aatgtgttcc ttcagcaaca ccacaaccac cac                                  2587

<210> SEQ ID NO 14
<211> LENGTH: 825
<212> TYPE: PRT
<213> ORGANISM: Mus sp.

<400> SEQUENCE: 14

Met Leu Gly Leu Trp Leu Leu Ser Val Leu Trp Thr Pro Val Ala Pro
1               5                   10                  15

Gly Pro Pro Leu Pro His Val Lys Gln Tyr Glu Val Val Trp Pro Arg
            20                  25                  30

Arg Leu Ala Ala Ser Arg Ser Arg Ala Leu Pro Ser His Trp Gly
        35                  40                  45

Gln Tyr Pro Glu Ser Leu Ser Tyr Ala Leu Gly Thr Ser Gly His Val
    50                  55                  60

Phe Thr Leu His Leu Arg Lys Asn Arg Asp Leu Leu Gly Ser Ser Tyr
65                  70                  75                  80

Thr Glu Thr Tyr Ser Ala Ala Asn Gly Ser Glu Val Thr Glu Gln Leu
                85                  90                  95

Gln Glu Gln Asp His Cys Leu Tyr Gln Gly His Val Glu Gly Tyr Glu
            100                 105                 110

Gly Ser Ala Ala Ser Ile Ser Thr Cys Ala Gly Leu Arg Gly Phe Phe
        115                 120                 125

Arg Val Gly Ser Thr Val His Leu Ile Glu Pro Leu Asp Ala Asp Glu
    130                 135                 140

Glu Gly Gln His Ala Met Tyr Gln Ala Lys His Leu Gln Gln Lys Ala
145                 150                 155                 160

Gly Thr Cys Gly Val Lys Asp Thr Asn Leu Asn Asp Leu Gly Pro Arg
                165                 170                 175

Ala Leu Glu Ile Tyr Arg Ala Gln Pro Arg Asn Trp Leu Ile Pro Arg
            180                 185                 190

Glu Thr Arg Tyr Val Glu Leu Tyr Val Val Ala Asp Ser Gln Glu Phe
        195                 200                 205

Gln Lys Leu Gly Ser Arg Glu Ala Val Arg Gln Arg Val Leu Glu Val
    210                 215                 220

Val Asn His Val Asp Lys Leu Tyr Gln Glu Leu Ser Phe Arg Val Val
225                 230                 235                 240

Leu Val Gly Leu Glu Ile Trp Asn Lys Asp Lys Phe Tyr Ile Ser Arg
                245                 250                 255

Tyr Ala Asn Val Thr Leu Glu Asn Phe Leu Ser Trp Arg Glu Gln Asn
            260                 265                 270

Leu Gln Gly Gln His Pro His Asp Asn Val Gln Leu Ile Thr Gly Val
        275                 280                 285

Asp Phe Ile Gly Ser Thr Val Gly Leu Ala Lys Val Ser Ala Leu Cys
    290                 295                 300

Ser Arg His Ser Gly Ala Val Asn Gln Asp His Ser Lys Asn Ser Ile
305                 310                 315                 320

Gly Val Ala Ser Thr Met Ala His Glu Leu Gly His Asn Leu Gly Met
                325                 330                 335

Ser His Asp Glu Asp Ile Pro Gly Cys Tyr Cys Pro Glu Pro Arg Glu
            340                 345                 350
```

```
Gly Gly Gly Cys Ile Met Thr Glu Ser Ile Gly Ser Lys Phe Pro Arg
            355                 360                 365

Ile Phe Ser Arg Cys Ser Lys Ile Asp Leu Glu Ser Phe Val Thr Lys
    370                 375                 380

Pro Gln Thr Gly Cys Leu Thr Asn Val Pro Asp Val Asn Arg Phe Val
385                 390                 395                 400

Gly Gly Pro Val Cys Gly Asn Leu Phe Val Glu His Gly Glu Gln Cys
                405                 410                 415

Asp Cys Gly Thr Pro Gln Asp Cys Gln Asn Pro Cys Cys Asn Ala Thr
            420                 425                 430

Thr Cys Gln Leu Val Lys Gly Ala Glu Cys Ala Ser Gly Thr Cys Cys
        435                 440                 445

His Glu Cys Lys Val Lys Pro Ala Gly Glu Val Cys Arg Leu Ser Lys
    450                 455                 460

Asp Lys Cys Asp Leu Glu Glu Phe Cys Asp Gly Arg Lys Pro Thr Cys
465                 470                 475                 480

Pro Glu Asp Ala Phe Gln Gln Asn Gly Thr Pro Cys Pro Gly Gly Tyr
                485                 490                 495

Cys Phe Asp Gly Ser Cys Pro Thr Leu Ala Gln Gln Cys Arg Asp Leu
            500                 505                 510

Trp Gly Pro Gly Ala Arg Val Ala Ala Asp Ser Cys Tyr Thr Phe Ser
        515                 520                 525

Ile Pro Pro Gly Cys Asn Gly Arg Met Tyr Ser Gly Arg Ile Asn Arg
    530                 535                 540

Cys Gly Ala Leu Tyr Cys Glu Gly Gly Gln Lys Pro Leu Glu Arg Ser
545                 550                 555                 560

Phe Cys Thr Phe Ser Ser Asn His Gly Val Cys His Ala Leu Gly Thr
                565                 570                 575

Gly Ser Asn Ile Asp Thr Phe Glu Leu Val Leu Gln Gly Thr Lys Cys
            580                 585                 590

Glu Glu Gly Lys Val Cys Met Asp Gly Ser Cys Gln Asp Leu Arg Val
        595                 600                 605

Tyr Arg Ser Glu Asn Cys Ser Ala Lys Cys Asn Asn His Gly Val Cys
    610                 615                 620

Asn His Lys Arg Glu Cys His Cys His Lys Gly Trp Ala Pro Pro Asn
625                 630                 635                 640

Cys Val Gln Arg Leu Ala Asp Val Ser Asp Glu Gln Ala Ala Ser Thr
                645                 650                 655

Ser Leu Pro Val Ser Val Val Val Leu Val Ile Leu Val Ala Ala Ala
            660                 665                 670

Met Val Ile Val Ala Gly Ile Val Ile Tyr Arg Lys Ala Pro Arg Gln
        675                 680                 685

Ile Gln Arg Arg Ser Val Ala Pro Lys Pro Ile Ser Gly Leu Ser Asn
    690                 695                 700

Pro Leu Phe Tyr Thr Arg Asp Ser Ser Leu Pro Ala Lys Asn Arg Pro
705                 710                 715                 720

Pro Asp Pro Ser Glu Thr Val Ser Thr Asn Gln Pro Pro Arg Pro Ile
                725                 730                 735

Val Lys Pro Lys Arg Pro Pro Ala Pro Pro Gly Ala Val Ser Ser
            740                 745                 750

Ser Pro Leu Pro Val Pro Val Tyr Ala Pro Lys Ile Pro Asn Gln Phe
            755                 760                 765
```

-continued

```
Arg Pro Asp Pro Pro Thr Lys Pro Leu Pro Glu Leu Lys Pro Lys Gln
    770                 775                 780

Val Lys Pro Thr Phe Ala Pro Pro Thr Pro Pro Val Lys Pro Gly Thr
785                 790                 795                 800

Gly Gly Thr Val Pro Gly Ala Thr Gln Gly Ala Gly Gly Pro Lys Val
                805                 810                 815

Ala Leu Lys Val Pro Ile Gln Lys Arg
            820                 825
```

<210> SEQ ID NO 15
<211> LENGTH: 5
<212> TYPE: PRT
<213> ORGANISM: Homo sapiens
<220> FEATURE:
<221> NAME/KEY: misc_feature
<222> LOCATION: (3)..(4)
<223> OTHER INFORMATION: Xaa means an arbitrary amino acid.

<400> SEQUENCE: 15

His Glu Xaa Xaa His
1               5

<210> SEQ ID NO 16
<211> LENGTH: 21
<212> TYPE: DNA
<213> ORGANISM: Mus sp.

<400> SEQUENCE: 16
gctccagatc ccatcatgct t                                      21

<210> SEQ ID NO 17
<211> LENGTH: 20
<212> TYPE: DNA
<213> ORGANISM: Mus sp.

<400> SEQUENCE: 17
gtggtggttg tggtgttgct                                        20

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 18
gctctagacc atgcttggcc tctggctgct c                           31

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 19
gctctagagg ggtgccctag ctggtcacc                              29

<210> SEQ ID NO 20
<211> LENGTH: 2021
<212> TYPE: DNA
<213> ORGANISM: Artificial Sequence
<220> FEATURE:

<223> OTHER INFORMATION: Description of Artificial Sequence: a sequence
      containing a promoter sequence of human MD8 gene

<400> SEQUENCE: 20

```
aggcgaggtt gggagaaagg atagctagaa caggatcctg cggggaacaa gggtgtgggc      60
agctctcacc cggggctgcc tcactgagag caccgccgag tggggtgggg ggtgtccaac     120
tctccagcca caaaccgctt cctccttgtc tgcaggctgt gcaggtctgg cctgtgagta     180
aacacattta tcagcaaccc aagctgtcag tctcagtgtt gtgcaaatgc cggaccggtg     240
agcagaggag cctgctagct ttcctgcctg gccccgaggc ccagaaaccc ctgatcttgt     300
gtcctgggt ctgggaagcc ctgggccttg agaagtgggg tttgcaggtg gtgacaggag      360
gaggggaggg aagcctccag ggctgtgggg ttcaggctcc cagaccccccc ggcacctgct    420
gaagaggaga gctgtgttct gtgggattgg gtggaacttc ctcagcgcgg gaggagcctg     480
ttctggccca agctggtcct gtcttttag gaataaatcc ctggtagctc agcgtcggca      540
ggggccttgc tgtgcctctg atgtggccag cgtgccgcct ttgcactttg ctgttgagta     600
acttgcacca tgaggtcaag gaagggaagt gtgattgcca gctggccatt gttctataat     660
aacagggtca cctgcatgag ctcaggcaca ggccagtatc cccagcccta cctgggagcc    720
tctcggcagc ctgggggacc tcgtcctgtg ccacacaggc aagcggacac accccccaggc   780
agcagaagtc acctgcggcc cagtgccagc ccttgctttc ttgcttttca tgccattcac     840
attagggtaa gaatggcttt gagacaaaat gtgacagcat cactcacgcc agcttagatc     900
ctccgggttc cctgtcctcc caggataacg tccgaggccg cggcctcttc ttgccactgc     960
cccttgacct ctgtcctctg cccctaggcc cgtgcagttc cctgactcgc cctgccctgg    1020
tgccctctct ccaggcagga ctccctccag ccccttgctg gccctgccct gcctctcccc    1080
agggaggccc tgagggcccc cccccccatg tgatctgtca gcagcgccct gtgtggtcat    1140
ctgagctgcc tttcctgcca ccaccactgt tcccaccccca ggagggcggc ctggctgtga  1200
aagccccagg gaggggtcct gggtggaccg tctgggagc tgtggtgtca gcccaaacct     1260
gcaccctcga ggctgagccc accacggggga atgtggtcac caagggcaag cacgcttggc  1320
cgcaggcctg gagacgccgg agccaggcca cggtgggctg ctgcaggctt tggtccacgt    1380
cggccagcgt cagctgctgt ctggggatct taggctaggg acggcccctg cacctgccat    1440
cacctgggct gggaccccca cctagggctc cccctcccca cttggacgcc tgcgggccca    1500
tgcctatccc actccggtga ggcctcagcc tggtggaggg ggcgcaggct tggggggag     1560
ggtggcagag cttcccacag ggctgaacct atgcccacaa agccatgact tgcccctgcc   1620
tgaggctttc tgttccccag gaaatcagag accccctctc ctgaaaccgc caggcggccc   1680
tcacaagtcc cttcccctcc aggacctgcc tggcgccacc tccttccagc cgccgggtcc   1740
ttcgagaggc cccctctcgg ggctctggcc ggacttggga caggctgtgc ctgagtttcc   1800
tcacctgtgc aagggaggat gctggattgt ggggagaggg gaaacggacc ccgcccccag   1860
gtgccgcgcg ccccgcccct cccaccggcc gaggggccca ttggctgcgg ggcgccgggg   1920
cggggcgcgc ggaaaagagc ctcgggccag gagcgcagga accagaccgt gtcccgcggg   1980
gctgtcacct ccgcgtgtgc tccccgaccc ggccaagctt t                       2021
```

<210> SEQ ID NO 21
<211> LENGTH: 28
<212> TYPE: DNA
<213> ORGANISM: Homo sapiens

```
<400> SEQUENCE: 21
aggcgaggtt gggagaaagg atagctag                                          28

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 22
aaagcttggc cgggtcgggg agca                                              24

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 23
gaagatctgc catgcgcggc ctcgggctc                                         29

<210> SEQ ID NO 24
<211> LENGTH: 33
<212> TYPE: DNA
<213> ORGANISM: Artificial sequence
<220> FEATURE:
<223> OTHER INFORMATION: Description of Artificial Sequence: an
      artificially synthesized primer sequence

<400> SEQUENCE: 24
gaagatctac ttgtcatcgt cgtccttgta gtc                                    33

<210> SEQ ID NO 25
<211> LENGTH: 37
<212> TYPE: DNA
<213> ORGANISM: artificial sequence
<220> FEATURE:
<223> OTHER INFORMATION: Description of Artificial Sequence: an
      artificially synthesized primer sequence

<400> SEQUENCE: 25
gctctagacc atggtgttgc tcaccgcggt cctcctg                                37

<210> SEQ ID NO 26
<211> LENGTH: 35
<212> TYPE: DNA
<213> ORGANISM: artificial sequence
<220> FEATURE:
<223> OTHER INFORMATION: Description of Artificial Sequence: an
      artificially synthesized primer sequence

<400> SEQUENCE: 26
cgggatccct caacgttgct gctgtcgaag gtgtg                                  35
```